(12) United States Patent
Lin et al.

(10) Patent No.: US 9,289,467 B2
(45) Date of Patent: Mar. 22, 2016

(54) COMPOSITIONS AND METHODS FOR TREATING BONE CONDITIONS

(75) Inventors: Feng Lin, Willoughby, OH (US); James E. Dennis, Cleveland Heights, OH (US); Zhidan Tu, Cleveland, OH (US)

(73) Assignee: Case Western Reserve University, Cleveland, OH (US)

(*) Notice: Subject to any disclaimer, the term of this patent is extended or adjusted under 35 U.S.C. 154(b) by 0 days.

(21) Appl. No.: 13/572,141

(22) Filed: Aug. 10, 2012

(65) Prior Publication Data

US 2013/0202612 A1 Aug. 8, 2013

Related U.S. Application Data

(60) Provisional application No. 61/521,874, filed on Aug. 10, 2011.

(51) Int. Cl.

| | |
|---|---|
| *A61K 39/00* | (2006.01) |
| *A61K 39/395* | (2006.01) |
| *A61K 38/17* | (2006.01) |
| *A61K 31/7088* | (2006.01) |
| *A61K 31/713* | (2006.01) |
| *C07K 16/18* | (2006.01) |

(52) U.S. Cl.
CPC ......... *A61K 38/1725* (2013.01); *A61K 31/7088* (2013.01); *A61K 31/713* (2013.01); *A61K 38/177* (2013.01); *A61K 39/3955* (2013.01); *C07K 16/18* (2013.01)

(58) Field of Classification Search
None
See application file for complete search history.

(56) References Cited

U.S. PATENT DOCUMENTS

| | | | |
|---|---|---|---|
| 4,692,511 A | | 9/1987 | Hahn |
| 5,393,763 A | * | 2/1995 | Black et al. ................... 514/333 |
| 5,480,974 A | | 1/1996 | Morgan et al. |
| 5,614,370 A | | 3/1997 | Konteatis et al. |
| 5,807,824 A | | 9/1998 | Oostrum et al. |
| 5,942,405 A | * | 8/1999 | Ames et al. ................... 435/7.24 |
| 6,723,743 B1 | | 4/2004 | Thurkauf et al. |
| 6,777,422 B2 | | 8/2004 | Lee et al. |
| 6,821,950 B1 | | 11/2004 | Fairlie et al. |
| 6,884,815 B1 | | 4/2005 | Thurkauf et al. |
| 7,148,225 B2 | | 12/2006 | Gao et al. |
| 7,169,775 B2 | | 1/2007 | Thurkauf et al. |
| 7,186,734 B2 | | 3/2007 | Maynard et al. |
| 7,271,270 B2 | | 9/2007 | Thurkauf et al. |
| 7,291,621 B2 | | 11/2007 | Gao et al. |
| 7,425,622 B2 | | 9/2008 | Rosen |
| 7,429,666 B2 | | 9/2008 | Lachance et al. |
| RE41,287 E | | 4/2010 | Fairlie et al. |
| 7,727,960 B2 | | 6/2010 | Hummel et al. |
| 7,919,459 B2 | | 4/2011 | Taylor et al. |
| 8,007,767 B2 | | 8/2011 | Thurkauf et al. |
| 8,183,363 B2 | * | 5/2012 | Karras ............................ 536/24.5 |
| 8,486,662 B2 | * | 7/2013 | Gelinas et al. ............... 435/69.6 |

OTHER PUBLICATIONS

"JPE-1375," www.amdbook.org/content/jpe1375-inhibits-c5-dry-amd-intravitreal, accessed Sep. 9, 2013.*
"SB-20-157," www.emdmillipore.com/life-science-research/sb-290157/EMD_BIO-559410/p_awyb.s1LIMEAAAEWIWEfVhTm, accessed Sep. 9, 2013).*
Bhole et al. (2003, Crit. Care Med. 31:S97-S103).*
Ignatius et al., 2011, J. Cell. Biochem. 112:2594-2605.*
Tu et al., Aug. 2010, Blood 116:4456-4463.*
Baelder et al., 2005, J. Immunol. 174:783-789.*
Ames, Robert S., et al., "Identification of a Selective Nonpeptide Antagonist of the Anaphylatoxin C3a Receptor that Demonstrates Antiinflammatory Activity in Animal Models", J. Immunol 2001: 166:6341-6348.
Fung, M., et al., "Pre-Naturalization of C5s-mediated effects by the monoclonal antibody 137-26 reacting with the C5a moiety of native C5 without preventing C5 cleavage", Clin Exp Immunol 2003; 133:160-169.
Heller, Tanja, et al., "Selection of a C5a Receptor Antagonist from Phase Libraries Attenuating the Inflammatory Response in Immune Complex Disease and Ischemia/Reperfusion Injury", J Immunol 1999; 163: 985-984.
Kaneko, Y., et al., "Antagonistic peptides against human anaphylatoxin C5a", Immunology 1995 86 149-154.
Mizuno, Masashi, et al., "Inhibition of a Membrane Complement Regulatory Protein by a monoclonal antibody induces acute lethal shock in rats primed with lipopolysaccharide", The Journal of Immunology, 1999, 162: 5477-5482.
Mocco, J., et al., "Complement Component C3 Mediates Inflammatory Injury Following Focal Cerebral Ischemia", Circ Res. 2006;99:209-217.
Otto, Magnus, et al., "C5a Mutants are Potent Antagonists of the C5a Receptor (CD88) and of C5L2", The Journal of Biological Chemistry, vol. 279, No. 1, Issue of Jan. 2, pp. 142-15, 2004.
Pellas, Theodore C., et al., "NOvel C5a Receptor Antagonists Regulate Neutrophil Functions in Vitro and In vivo", J Immunol 1998; 160:5616-5612.

(Continued)

*Primary Examiner* — Elizabeth C Kemmerer
(74) *Attorney, Agent, or Firm* — Tarolli, Sundheim, Covell & Tummino LLP

(57) ABSTRACT

A method of treating a degenerative bone condition of a subject includes administering to hematopoietic progenitor cells or osteoclast progenitor cells of the subject at least one agent that substantially reduces the interaction of at least one of C3a or C5a with the C3a receptor (C3aR) and/or C5a receptor (C5aR), a STAT3/IL-6 signaling pathway antagonist, and a combination thereof, the agent being administered to the hematopoietic progenitor cells or osteoclast progenitor cells at an amount effective to inhibit osteoclast differentiation of hematopoietic progenitor cells or osteoclast progenitor cells.

18 Claims, 6 Drawing Sheets

(56) References Cited

OTHER PUBLICATIONS

Short, Anna, et al., "Effects of a new C5a receptor antagonist on C5- and endotoxin-induced neutropenia in the rat", British Journal of Pharmacology (1999) 125, 551-554.

Sumichika, Hiroshi, et al., "Identification of a Potent and Orally Active Non-Peptide C5a Receptor Antagonist", The Journal of Biological Chemistry, vol. 277, No. 51, Issue of Dec. 20, pp. 49403-49407, 2002.

Tsuji, Ryohei F., et al., "Preferntial Suppression of Delayed- type Hypersensitivity by L-156,602, a C5a Receptor Antagonist", Biosci. Biochem. 56 (10), 1686-1689, 1992.

Zhang, Xiaolu, et al., "Solution structure of a unique C5a semi-synthetic antagonist: Implications in receptor binding", Protein Science (1997), 6:65-72. Cambridge University Press.

* cited by examiner

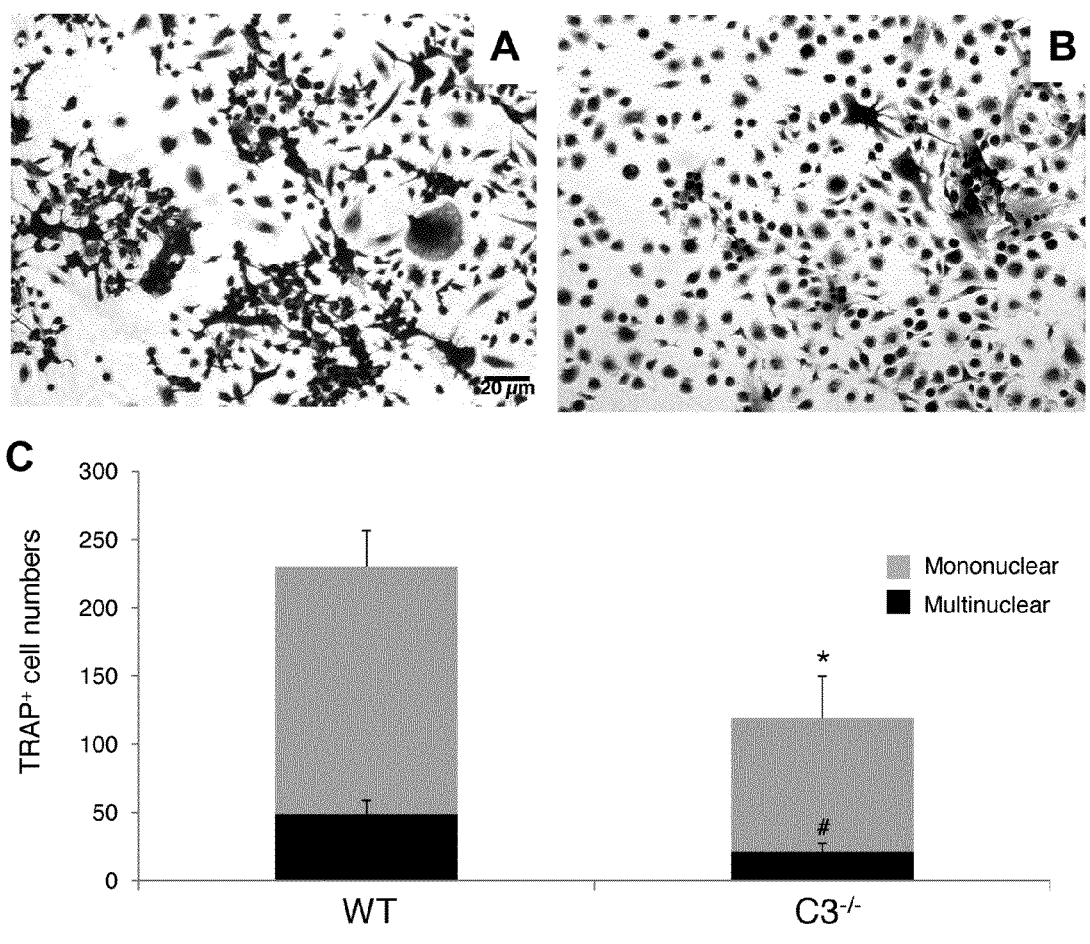
Figs. 3A-C

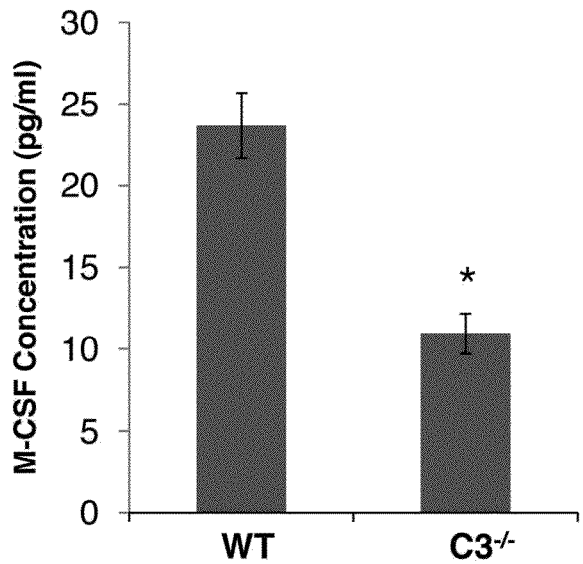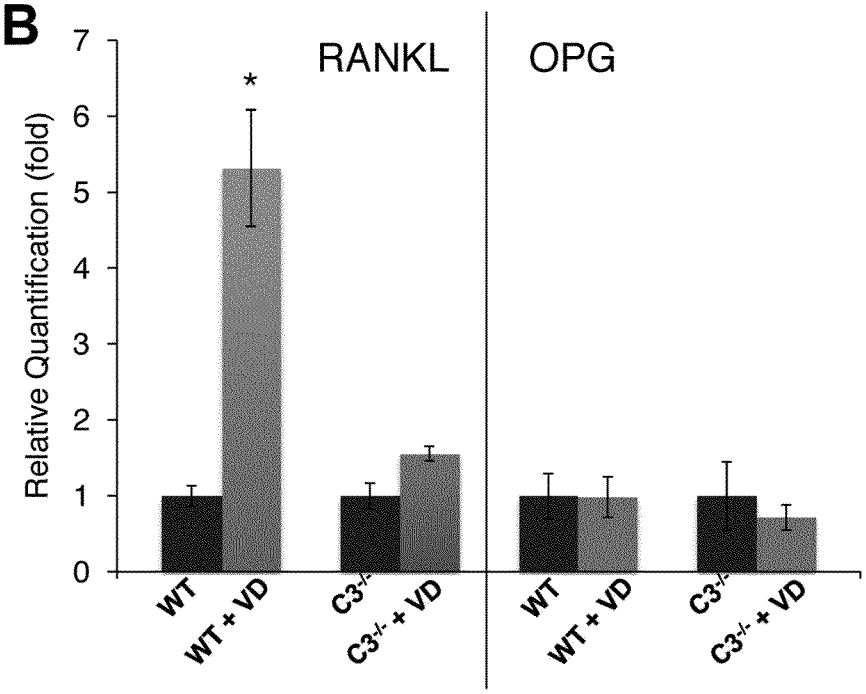
Figs. 4A-B

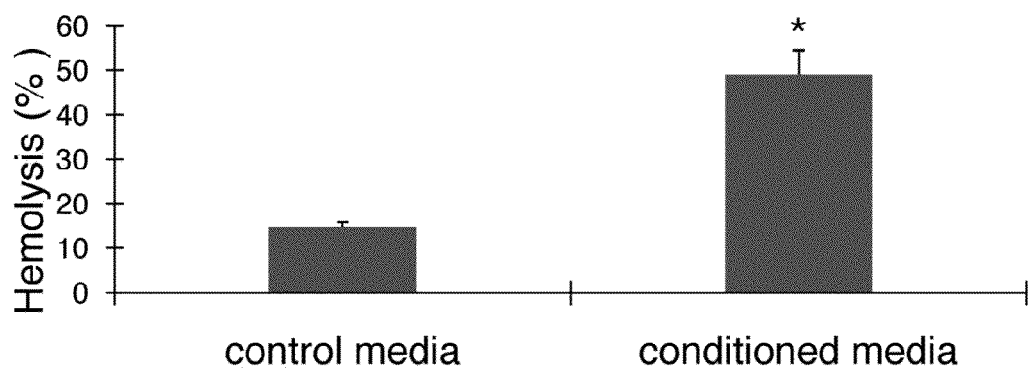
Fig. 5
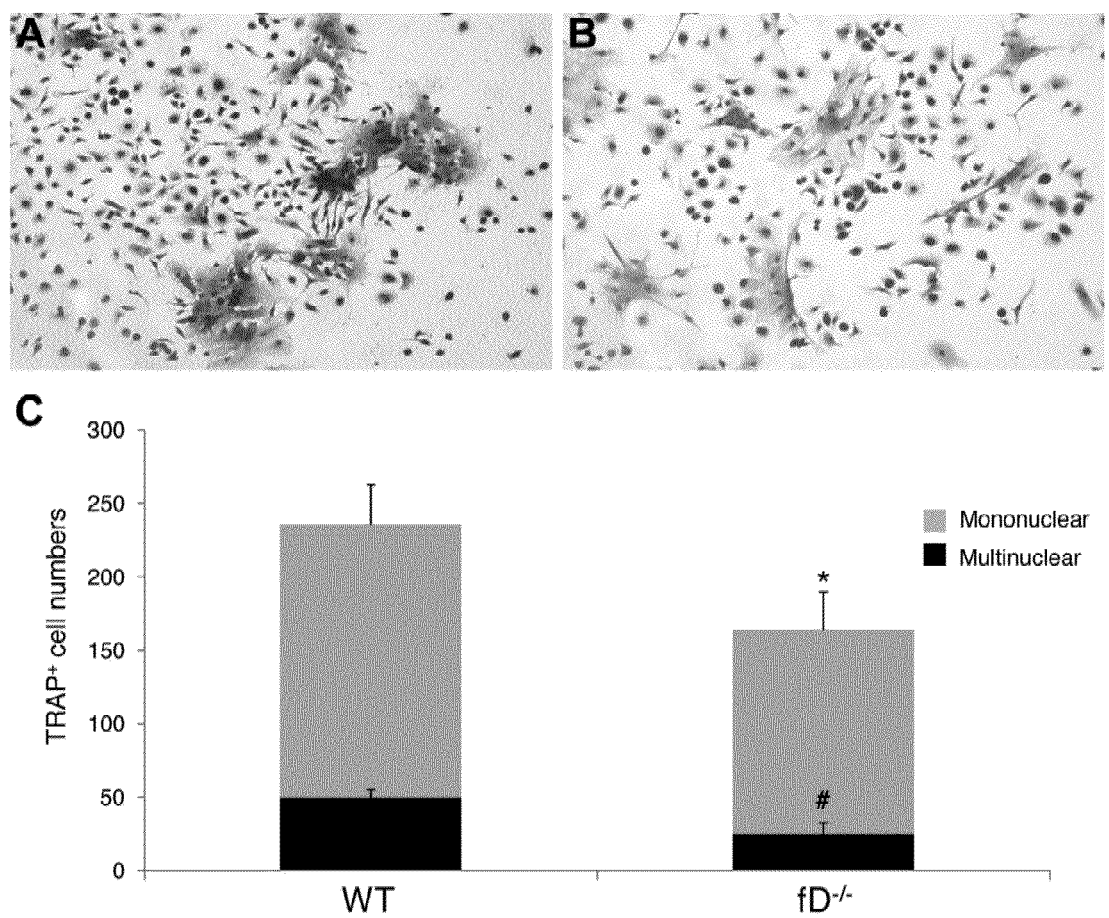
Figs. 6A-C

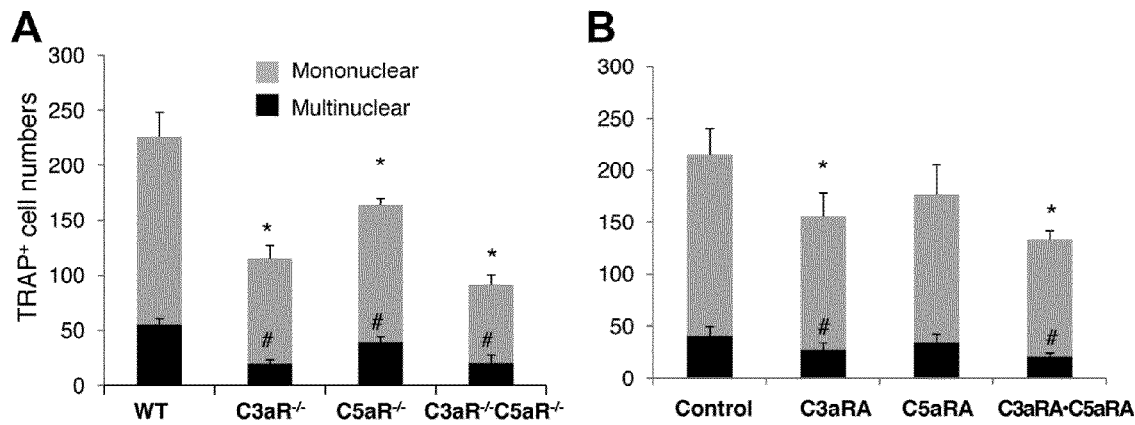
Figs. 7A-B
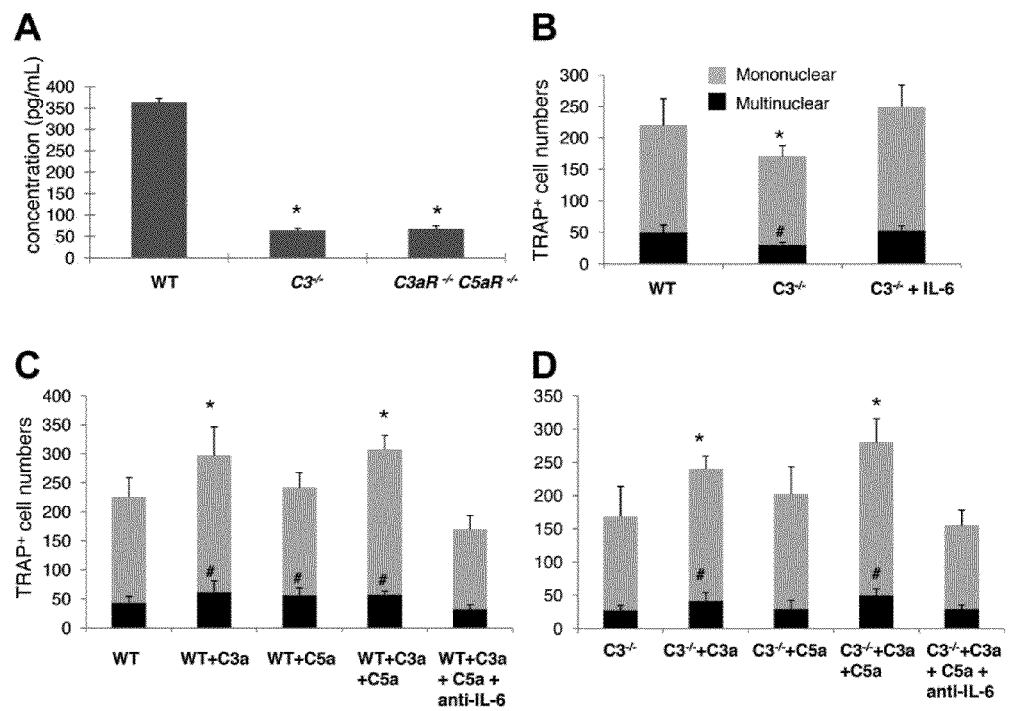
Figs. 8A-D

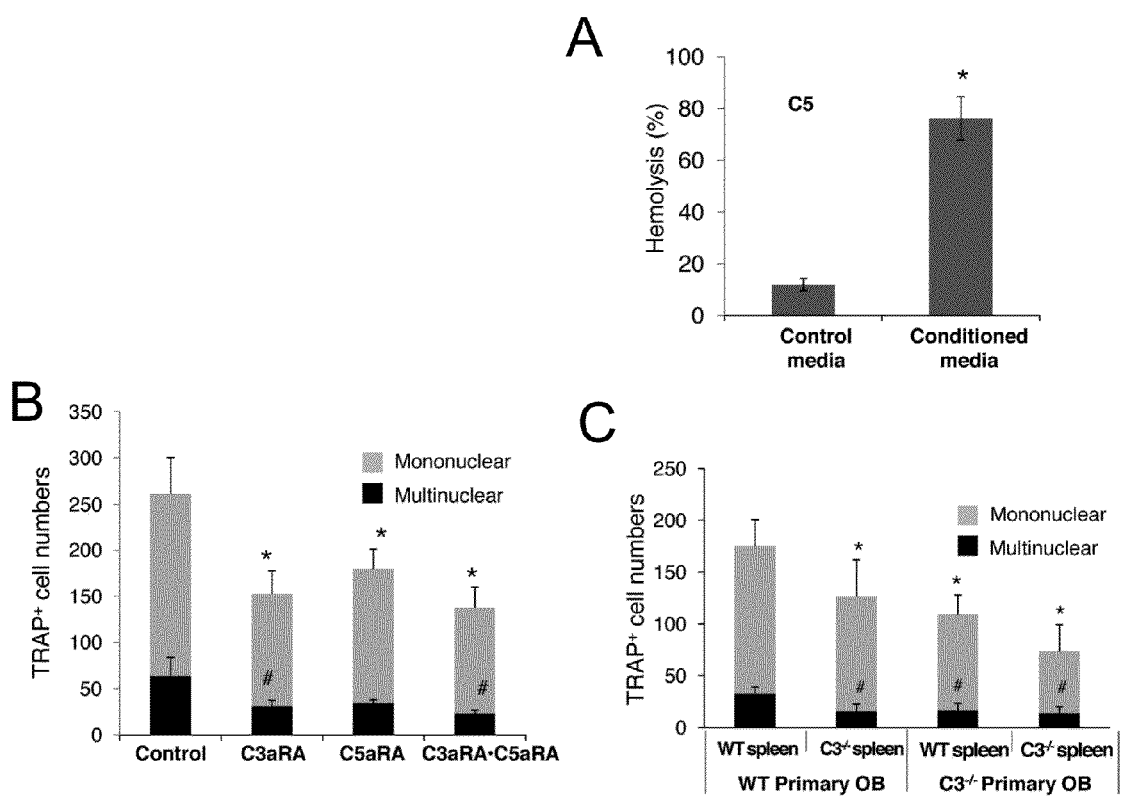
Figs. 9A-C

COMPOSITIONS AND METHODS FOR TREATING BONE CONDITIONS

RELATED APPLICATION

This application claims priority from U.S. Provisional Application No. 61/521,874, filed Aug. 10, 2011, the subject matter of which is incorporated herein by reference in its entirety.

GOVERNMENT FUNDING

This invention was made with government support under Grant No. 5R01NS052471 awarded by The National Institute of Neurological Disorders and Stroke (NINDS). The United States government may have certain rights to the invention.

TECHNICAL FIELD

This application relates to compositions and methods of treating bone conditions, and particularly relates to compositions and methods of treating osteoporosis and/or osteopenia.

BACKGROUND

Osteoporosis and particularly osteoporosis-related fractures are a major health problem in the United States. Approximately 10 million Americans are at risk for osteoporosis-related fractures and there are an estimated 1.5 million osteoporosis-related fractures per year. While there are several currently-approved therapies for the treatment of osteoporosis, including bisphosphonates, calcitonin, estrogen, selective estrogen receptor modulators (SERMS) and intermittent parathyroid hormone (PTH) treatments, each of these has drawbacks. Estrogen treatment or hormone replacement therapy has fallen out of favor due to the increased risk of breast cancer. There are a range of bisphosphonates available that show relatively good tolerance, but there remain issues with respect to osteonecrosis of the jaw, atypical bone fragility, gastrointestinal discomfort and some cases of influenza-like illnesses. Importantly, while most bisphosphonates show good to excellent efficacy for decreasing vertebral fracture risk, none of the bisphosphonate treatments shows particularly good efficacy in preventing peripheral fractures (<30% decrease in risk). Calcitonin treatments are limited because they have yet to show a reduction in non-vertebral fracture risk. PTH is the only approved anabolic treatment for osteoporosis and is the only treatment that is moderately effective for reducing peripheral fracture risk, but there is an increased risk of osteosarcoma which limits PTH treatments to no more than 2 years. Because of lingering issues of side effects and clinical efficacy, significant efforts continue to be made in an attempt to develop more effective drugs for treating or preventing osteoporosis.

SUMMARY

This application relates to a method of treating a degenerative bone condition of a subject. The method includes administering to hematopoietic progenitor cells or osteoclast progenitor cells of the subject at least one agent that substantially reduces the interaction of at least one of C3a or C5a with the C3a receptor (C3aR) and/or C5a receptor (C5aR), a STAT3/IL-6 signaling pathway antagonist, and a combination thereof. The agent can be administered to the hematopoietic progenitor cells or osteoclast progenitor cells at an amount effective to inhibit osteoclast differentiation of hematopoietic progenitor cells or osteoclast progenitor cells.

In some embodiments, the agent can include at least one complement antagonist selected from the group consisting of a small molecule, a polypeptide, and a polynucleotide. The at least one complement antagonist can be selected from the group consisting of DAF or an antibody directed against at least one of C3, C5, C3 convertase, C5 convertase, C3a, C5a, C3aR, or C5aR. The at least one complement antagonist can also be a small interfering RNA directed against a polynucleotide encoding at least one of C3, C5, C3aR, or C5aR.

In other embodiments, the at least one complement antagonist can include an antibody directed against C5aR and an antibody directed against C3aR, an antibody directed against C5a and an antibody directed against C3a, and/or an antibody directed against C5 and an antibody directed against C3.

In some embodiments, the agent can be administered to the hematopoietic progenitor cells or osteoclast progenitor cells in vitro. In other embodiments, the agent be administered locally to the hematopoietic progenitor cells or osteoclast progenitor cells at the site of the bone condition. The agent can also be conjugated to a targeting moiety that targets hematopoietic progenitor cells or osteoclast progenitor cells.

In some embodiments, the degenerative bone condition can include osteopenia or osteoporosis, such as post-menopausal osteopenia or post-menopausla osteoporosis.

BRIEF DESCRIPTION OF THE DRAWINGS

FIG. 3(A-C) illustrates images showing illustrates TRAP-positive cells from (A) WT and (B)C3$^{-/-}$ BM cells produced from aliquots of $2 \times 10^6$ WT and C3$^{-/-}$ BM cells cultured in α-MEM/10% heat-inactivated FBS media in each well of a 24-well plate together with $1 \times 10^{-8}$M 1.25(OH)$_2$ vitamin D$_3$; and (C) a graph showing total mononuclear (mono)/multinucleated (multi) TRAP-positive cells in each well.

FIG. 4(A-B) illustrates graph showing C3-deficient BM cells produce decreased amounts of M-CSF and failed to up-regulate RANKL during differentiation. (A) M-CSF levels were measured by ELISA in WT and C3$^{-/-}$ BM cell-conditioned media during differentiation. (B) RANKL/OPG expression levels were quantified by qRT-PCR in WT and C3$^{-/-}$ BM cells after 1.25(OH)2 vitamin D3 (VD) stimulation.

FIG. 5 illustrates a graph showing the hemolysis percent using C5-depleted sera plus 1:5 diluted control media or BM cell-conditioned mediaof an E$^{sha}$ hemolytic assay.

FIG. 6(A-C) illustrates images showing TRAP-positive cells from (A) WT and (B) factor D$^{-/-}$ BM cells of aliquots of $2 \times 10^6$ WT and factor D$^{-/-}$ BM cells cultured in α-MEM/10% heat-inactivated FBS media plate together with $1 \times 10^{-8}$M 1.25(OH)$_2$ vitamin D$_3$; and (C) a graph showing representative TRAP-positive cells from, and total mononuclear (mono)/multinucleated (multi) TRAP-positive cells in each well.

FIG. 7(A-B) illustrates: (A) TRAP-positive cells of $2 \times 10^6$ WT,C3aR$^{-/-}$,C5aR$^{-/-}$ and C3aR$^{-/-}$ C5aR$^{-/-}$ BM cells cultured in α-MEM/10% heat-inactivated media of a 24-well plate together with $1 \times 10^{-8}$M 1.25(OH)$_2$ vitamin D$_3$; and (B) TRAP-positive cells of WT BM cells ($2 \times 10^6$) cultured in α-MEM/10% heat-inactivated FBS media of a 24-well plate together with $1\times10^{-8}$M $1.25(OH)_2$ vitamin $D_3$ in the presence of placebo (control), C3aRA, C5aRA, or C3aRA•C5aRA.

FIG. 8(A-D) illustrates complement graphs showing: (A) quantification of IL-6 levels in supernatants cultured with WT, $C3^{-/-}$, and $C3aR^{-/-}$ $C5aR^{-/-}$ BM cells during differentiation. BM cells ($2\times10^6$) were cultured in differentiation media in each well of a 24-well plate together with $1\times10^{-8}$M $1.25(OH)_2$ vitamin, and IL-6 levels were measured in supernatants on day 1; (B) supplementing IL-6 into $C3^{-/-}$ BM cell cultures restored their OC differentiation capabilities; (C) exogenous C3a/C5a augmented OC differentiation from WT BM cells, while neutralization of IL-6 abolished the stimulating effect; and (D) exogenous C3a/C5a augmented OC differentiation from $C3^{-/-}$ BM cells, while neutralization of IL-6 abolished the stimulating effect.

FIG. 9(A-C) illustrates graphs showing (A) EshA-hemolytic assays using C5-depleted sera plus 1:5 diluted control media or BM cell-conditioned media, showing that BM cell-conditioned media compensated the absence of C5, therefore inducing C5b-9—mediated hemolysis; (B) human BM cells were incubated with $1\times10^{-8}$M $1.25(OH)_2$ vitamin $D_3$ in the presence of placebo (control), C3aRA, C5aRA, or C3aRA•C5aRA, showing that efficient OC differentiation in humans also requires C3aR/C5aR as in mice. Representative results of 2 independent experiments; and (C) Both mesenchymal cells and OC progenitors are involved in the complement-regulated OC differentiation. Samples of $2\times10^4$ primary WT or $C3^{-/-}$ calvarial OBs were cultured with $2\times10^6$ WT and $C3^{-/-}$ splenocytes (as source of OC progenitors) together with $1\times10^{-8}$M $1.25(OH)_2$ vitamin $D_3$.

DETAILED DESCRIPTION

Figure 1:
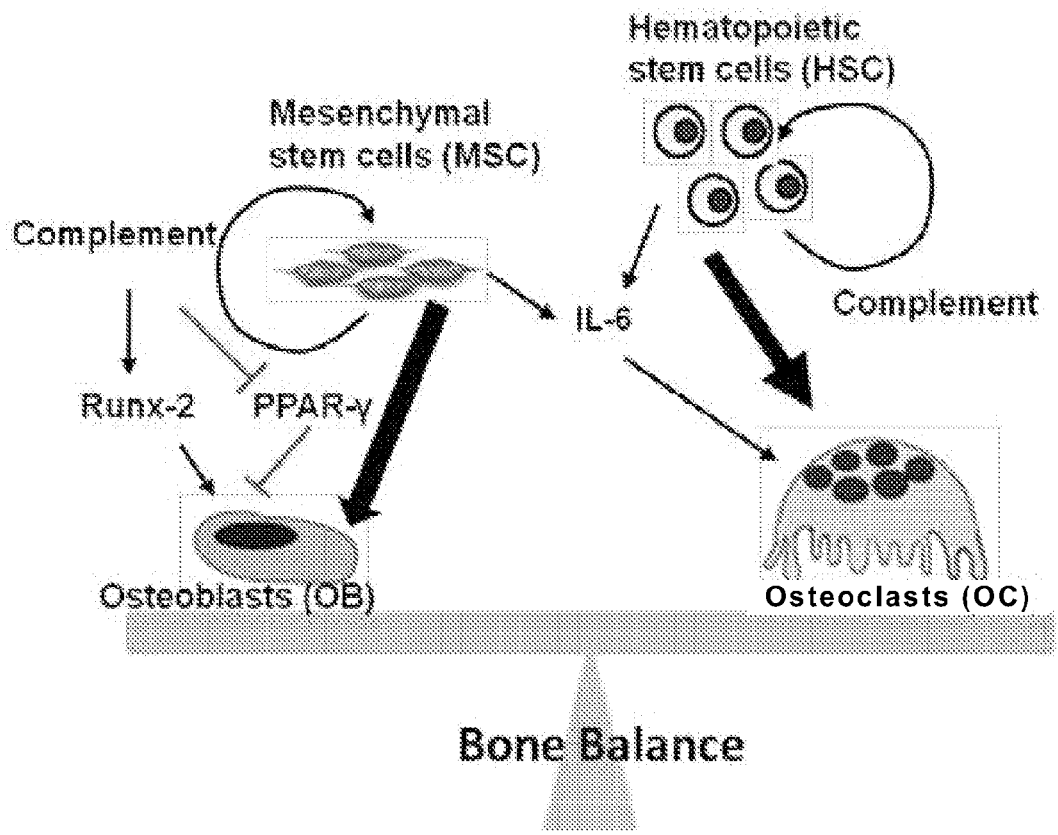
FIG. 1 is a schematic illustration showing that complement regulates bone balance in osteoporosis by modulating OC and OB differentiation.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994. The definitions provided herein are to facilitate understanding of certain terms used frequently herein and are not meant to limit the scope of the application described herein.

As used herein, the term "polypeptide" refers to an oligopeptide, peptide, or protein sequence, or to a fragment, portion, or subunit of any of these, and to naturally occurring or synthetic molecules. The term "polypeptide" also includes amino acids joined to each other by peptide bonds or modified peptide bonds, i.e., peptide isosteres, and may contain any type of modified amino acids. The term "polypeptide" also includes peptides and polypeptide fragments, motifs and the like, glycosylated polypeptides, and all "mimetic" and "peptidomimetic" polypeptide forms.

As used herein, the term "polynucleotide" refers to oligonucleotides, nucleotides, or to a fragment of any of these, to DNA or RNA (e.g., mRNA, rRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, siRNAs, microRNAs, and ribonucleoproteins. The term also encompasses nucleic acids, i.e., oligonucleotides, containing known analogues of natural nucleotides, as well as nucleic acid-like structures with synthetic backbones.

As used herein, the term "antibody" refers to whole antibodies, e.g., of any isotype (IgG, IgA, IgM, IgE, etc.), and includes fragments thereof which are also specifically reactive with a target polypeptide. Antibodies can be fragmented using conventional techniques and the fragments screened for utility and/or interaction with a specific epitope of interest. Thus, the term includes segments of proteolytically-cleaved or recombinantly-prepared portions of an antibody molecule that are capable of selectively reacting with a certain polypeptide. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The term "antibody" also includes polyclonal, monoclonal, or other purified preparations of antibodies, recombinant antibodies, monovalent antibodies, and multivalent antibodies. Antibodies may be humanized, and may further include engineered complexes that comprise antibody-derived binding sites, such as diabodies and triabodies.

As used herein, the term "complementary" refers to the capacity for precise pairing between two nucleobases of a polynucleotide and its corresponding target molecule. For example, if a nucleobase at a particular position of a polynucleotide is capable of hydrogen bonding with a nucleobase at a particular position of a target polynucleotide (the target nucleic acid being a DNA or RNA molecule, for example), then the position of hydrogen bonding between the polynucleotide and the target polynucleotide is considered to be complementary. A polynucleotide and a target polynucleotide are complementary to each other when a sufficient number of complementary positions in each molecule are occupied by nucleobases, which can hydrogen bond with each other. Thus, "specifically hybridizable" and "complementary" are terms which can be used to indicate a sufficient degree of precise pairing or complementarity over a sufficient number of nucleobases such that stable and specific binding occurs between a polynucleotide and a target polynucleotide.

As used herein, the term "subject" refers to any warm-blooded organism including, but not limited to, human beings, rats, mice, dogs, goats, sheep, horses, monkeys, apes, rabbits, cattle, etc.

As used herein, the terms "complement polypeptide" or "complement component" refer to a polypeptide (or a polynucleotide encoding the polypeptide) of the complement system that functions in the host defense against infections and in the inflammatory process. Complement polypeptides constitute target substrates for the complement antagonists provided herein.

As used herein, the term "complement antagonist" refers to a polypeptide, polynucleotide, or small molecule capable of substantially reducing or inhibiting the activity of a complement component.

A complement component can include any one or combination of interacting blood polypeptides or glycoproteins. There are at least 30 soluble plasma polypeptides, in addition to cell surface receptors, which can bind complement reaction products and which can occur on inflammatory cells and cells of the immune system. In addition, there are regulatory membrane proteins that can protect host cells from accidental complement attack. Complement components can include polypeptides that function in the classical pathway, such as C2, polypeptides that function in the alternative pathway, such as Factor B, and polypeptides that function in the lectin pathway, such as MASP-1.

Complement components can also include: any of the "cleavage products" (also referred to as "fragments") that are formed upon activation of the complement cascade; complement polypeptides that are inactive or altered forms of complement polypeptides, such as iC3 and C3a-desArg; and components indirectly associated with the complement cascade. Examples of such complement components can include, but are not limited to, C1q, C1r, C1s, C2, C3, C3a, C3b, C3c, C3dg, C3g, C3d, C3f, iC3, C3a-desArg, C4, C4a, C4b, iC4, C4a-desArg, C5, C5a, C5a-des-Arg, C6, C7, C8, C9, MASP-1, MASP-2, MBL, Factor B, Factor D, Factor H, Factor I, CR1, CR2, CR3, CR4, properdin, C1Inh, C4bp, MCP, DAF, CD59 (MIRL), clusterin, HRF, and allelic and species variants of any complement polypeptide.

As used herein, the terms "treatment," "treating," or "treat" refers to any specific method or procedure used for the cure of, inhibition of, prophylaxis of, reduction of, elimination of, or the amelioration of a bone condition or degenerative bone condition, such as osteopenia, osteoporosis, post-menopausal osteopenia, and post-menopausal osteoporosis.

As used herein, the term "effective amount" refers to a dosage of an agent described herein administered alone or in conjunction with any additional therapeutic agents that are effective and/or sufficient to provide treatment of a bone condition or degenerative bone condition, such as osteopenia, osteoporosis, post-menopausal osteopenia, and post-menopausal osteoporosis. The effective amount can vary depending on the subject, the disease being treated, and the treatment being affected.

As used herein, the term "therapeutically effective amount" refers to that amount of an agent described herein administered alone and/or in combination with additional therapeutic agents that results in amelioration of symptoms associated with a bone condition or degenerative bone condition, such as osteopenia, osteoporosis, post-menopausal osteopenia, and post-menopausal osteoporosis.

As used herein, the terms "parenteral administration" and "administered parenterally" refers to modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

As used herein, the terms "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

As used herein, "Unit dosage" formulations are those containing a dose or sub-dose of the administered ingredient adapted for a particular timed delivery. For example, exemplary "unit dosage" formulations are those containing a daily dose or unit or daily sub-dose or a weekly dose or unit or weekly sub-dose and the like.

Embodiments of this application relate to methods and compositions for modulating osteoclast (OC) and/or osteoblast (OB) differentiation and to methods and compositions for treating treat diseases, disorders, and conditions where inhibition and/or promotion of osteoclast differentiation and/or osteoblast differentiation is desired. The methods can include administering to osteoclast progenitors (e.g., hematopoietic progenitors or hematopietic stem cells) or osteoblast progenitors (e.g., mesenchymal stem cells) at least one agent that modulates (e.g., inhibits or promotes) C3aR and/or C5aR signaling of the cells.

It was found that complement deprivation has a protective effect on estrogen deficiency-driven osteoporosis in an animal model of post-menopausal osteoporosis, and that complement regulates mouse and human osteoclast (OC) and osteoblast (OB) differentiation through C3aR/C5aR-driven IL-6 production. The bone-resorbing OCs and the bone-forming OBs maintain the dynamic balance of bone. While OCs are differentiated from hematopoietic stem cells (HSCs), OBs are derived from mesenchymal stem (or stromal) cells (MSCs), and MSCs differentiate into OBs at the expense of other potential differentiation lineages, e.g. adipocytes. An array of factors including RANKL, OPG, IL-6, TNF-α and IL-1 regulate OC differentiation from HSCs, while Runx2 and PPAR-γ are the transcription factors that regulate MSC differentiation along the OB and adipocyte lineages. In post-menopause osteoporosis, both OC and OB numbers increase after estrogen deprivation. However, the increased OC numbers overwhelm the increased OB numbers, leading to net bone loss. Complement, locally produced by bone marrow (BM) cells, regulates both human and mouse OC differentiation through C3aR/C5aR-driven IL-6 production. C3aR and C5aR are the two receptors for the complement activation products C3a and C5a, which are expressed in a broad spectrum of cells. It was also found that $C3^{-/-}$ mice are protected from bone loss after ovariectomy (OVX) despite the in vitro results that $C3^{-/-}$ MSC have decreased capacity of differentiating to OBs in vitro, suggesting that complement has a major role in the regulation of skeletal homeostasis (FIG. 1) and that that C3aR and C5aR antagonists can be an effective treatment modality for osteoporosis. The complement system can therefore be use as a target for the treatment and prevention of a bone condition, such a degenerative bone condition including osteopenia, osteoporosis, post-menopausal osteopenia, post-menopausal osteoporosis and other degenerative bone conditions, such as in autoimmune arthritis.

Accordingly, based at least in part on these findings, in some embodiments of the application hematopoietic progenitor cells, such as hematopoietic stem cells, or osteoclast progenitor cells, for example, found in bone marrow, can be contacted (e.g., directly or locally) with a therapeutically effective amount of an agent that modulates (e.g., inhibits or promotes) C3aR and/or C5aR signaling of the cells and modulates (e.g., inhibits or promotes) osteoclast differentiation. .

In some embodiments, osteoclast differentiation of hematopoietic progenitor cells or osteoclast progenitor cells, can be inhibited by administering to the hematopoietic progenitor cells or osteoclast progenitor cells an agent that inhibits C3aR and/or C5aR signaling of the cells. The agent can be selected from the group consisting of a complement antagonist that inhibits or substantially reduces the interaction of at least one of C3a or C5a with the C3a receptor (C3aR) and C5a receptor (C5aR), an IL-6/STAT3 signaling pathway antagonist, and combinations thereof.

By inhibiting or substantially reducing the activity of a complement component, it is meant that the activity of the complement component may be entirely or partly diminished. For example, an inhibition or reduction in the functioning of a C3/C5 convertase may prevent cleavage of C5 and C3 into C5a and C3a, respectively. An inhibition or reduction in the functioning of C5, C3, C5a and/or C3a polypeptides may reduce or eliminate the ability of C5a and C3a to bind C5aR and C3aR, respectively. An inhibition or reduction in Factor B, Factor D, properidin, Bb, Ba and/or any other protein of the complement pathway that is used in the formation of C3 convertase, C5 convertase, C5, C3, C5a and/or C3a may reduce or eliminate the ability of C5a and C3a to be formed and bind to C5aR and C3aR, respectively. Additionally, an inhibition or reduction in the functioning of a C5aR or C3aR may similarly reduce or eliminate the ability of C5a and C3a to bind C5aR and C3aR, respectively.

In an aspect of the application, the at least one complement antagonist can include an antibody or antibody fragment directed against a complement component that can affect or inhibit the formation of C3a and/or C5a (e.g., anti-Factor B, anti-Factor D, anti-C5, anti-C3, ant-C5 convertase, and anti-C3 convertase) and/or reduce C5a/C3a-C5aR/C3aR interactions (e.g., anti-C5a, anti-C3a, anti-C5aR, and C3aR antibodies). In one example, the antibody or antibody fragment can be directed against or specifically bind to an epitope, an antigenic epitope, or an immunogenic epitope of a C5, C3, C3a, C5a, C5aR, C3aR, C5 convertase, and/or C3 convertase. The term "epitope" as used herein can refer to portions of C5, C3, C3a, C5a, C5aR, C3aR, C5 convertase, and/or C3 convertase having antigenic or immunogenic activity. An "immunogenic epitope" as used herein can include a portion of a C5, C3, C3a, C5a, C5aR, C3aR, C5 convertase, and/or C3 convertase that elicits an immune response in a subject, as determined by any method known in the art. The term "antigenic epitope" as used herein can include a portion of a polypeptide to which an antibody can immunospecifically bind as determined by any method well known in the art.

Examples of antibodies directed against C5, C3, C3a, C5a, C5aR, C3aR, C5 convertase, and/or C3 convertase are known in the art. For example, mouse monoclonal antibodies directed against C3aR can include those available from Santa Cruz Biotechnology, Inc. (Santa Cruz, Calif.). Monoclonal anti-human C5aR antibodies can include those available from Research Diagnostics, Inc. (Flanders, N.J.). Monoclonal anti-human/anti-mouse C3a antibodies can include those available from Fitzgerald Industries International, Inc. (Concord, Me.). Monoclonal anti-human/anti-mouse C5a antibodies can include those available from R&D Systems, Inc. (Minneapolis, Minn.).

In some embodiments, the complement antagonist can include a purified polypeptide that is a dominant negative or competitive inhibitor of C5, C3, C3a, C5a, C5aR, C3aR, C5 convertase, and/or C3 convertase. As used herein, "dominant negative" or "competitive inhibitor" refers to variant forms of a protein that inhibit the activity of the endogenous, wild type form of the protein (i.e., C5, C3, C3a, C5a, C5aR, C3aR, C5 convertase, and/or C3 convertase). As a result, the dominant negative or competitive inhibitor of a protein promotes the "off" state of protein activity. In the context of the present invention, a dominant negative or competitive inhibitor of C5, C3, C3a, C5a, C5aR, C3aR, C5 convertase, and/or C3 convertase is a C5, C3, C3a, C5a, C5aR, C3aR, C5 convertase, and/or C3 convertase polypeptide, which has been modified (e.g., by mutation of one or more amino acid residues, by posttranscriptional modification, by posttranslational modification) such that the C5, C3, C3a, C5a, C5aR, C3aR, C5 convertase, and/or C3 convertase inhibits the activity of the endogenous C5, C3, C3a, C5a, C5aR, C3aR, C5 convertase, and/or C3 convertase.

In some embodiments, the competitive inhibitor of C5, C3, C3a, C5a, C5aR, C3aR, C5 convertase, and/or C3 convertase can be a purified polypeptide that has an amino acid sequence, which is substantially similar (i.e., at least about 75%, about 80%, about 85%, about 90%, about 95% similar) to the wild type C5, C3, C3a, C5a, C5aR, C3aR, C5 convertase, and/or C3 convertase but with a loss of function. The purified polypeptide, which is a competitive inhibitor of C5, C3, C3a, C5a, C5aR, C3aR, C5 convertase, and/or C3 convertase, can be administered to a cell expressing C5aR and/or C3aR.

It will be appreciated that antibodies directed to other complement components used in the formation of C5, C3, C5a, C3a, C5 convertase, and/or C3 convertase can be used in accordance with the method described herein to reduce and/or inhibit interactions C5a and/or C3a with C5aR and C3aR. The antibodies can include, for example, known Factor B, properdin, and Factor D antibodies that reduce, block, or inhibit the formation of C5a and/or C3a.

In some embodiments, the complement antagonist can include RNA interference (RNAi) polynucleotides to induce knockdown of an mRNA encoding a complement component. For example, an RNAi polynucleotide can comprise a siRNA capable of inducing knockdown of an mRNA encoding a C3, C5, C5aR, or C3aR polypeptide.

RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner. Without being bound by theory, RNAi appears to involve mRNA degradation, however the biochemical mechanisms are currently an active area of research. Despite some mystery regarding the mechanism of action, RNAi provides a useful method of inhibiting gene expression in vitro or in vivo.

As used herein, the term "dsRNA" refers to siRNA molecules or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response.

As used herein, the term "RNAi construct" is a generic term used throughout the specification to include small interfering RNAs (siRNAs), hairpin RNAs, and other RNA species, which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (I) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences.

The choice of promoter and other regulatory elements generally varies according to the intended host cell. In general, expression vectors of utility in recombinant DNA techniques are often in the form of "plasmids" which refer to circular double stranded DNA loops, which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an RNAi construct can be modified with phosphorothioates, phosphoramidate, phosphodithioates, chimeric methylphosphonate-phosphodie- sters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) Proc Natl Acad Sci USA, 98:9742-9747; Elbashir, et al. (2001) EMBO J, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the Drosophila in vitro system is used. In this embodiment, dsRNA is combined with a soluble extract derived from Drosophila embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

Examples of a siRNA molecule directed to an mRNA encoding a C3a, C5a, C5aR, or C3aR polypeptide are known in the art. For instance, human C3a, C3aR, and C5a siRNA is available from Santa Cruz Biotechnology, Inc. (Santa Cruz, Calif.). Additionally, C5aR siRNA is available from Qiagen, Inc. (Valencia, Calif.). siRNAs directed to other complement components, including C3 and C5, are known in the art.

In other embodiments, the RNAi construct can be in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects, which may be caused by the sequence-independent dsRNA response.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52). Such hairpin RNAs are engineered in cells or in an animal to ensure continuous and stable suppression of a desired gene. It is known in the art that siRNAs can be produced by processing a hairpin RNA in the cell.

In yet other embodiments, a plasmid can be used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an exemplary vector for bi-directional transcription of a transgene to yield both sense and antisense RNA transcripts of the same transgene in a eukaryotic cell. Accordingly, in certain embodiments, the a recombinant vector can have the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in WO01/68836 and WO01/75164.

Examples RNAi constructs that specifically recognize a particular gene or a particular family of genes, can be selected using methodology outlined in detail above with respect to the selection of antisense oligonucleotide. Similarly, methods of delivery RNAi constructs include the methods for delivery antisense oligonucleotides outlined in detail above.

In some embodiments, a lentiviral vector can be used for the long-term expression of a siRNA, such as a short-hairpin RNA (shRNA), to knockdown expression of C5, C3, C5aR, and/or C3aR in hematopoietic stem cells or bone marrow cells. Although there have been some safety concerns about the use of lentiviral vectors for gene therapy, self-inactivating lentiviral vectors are considered good candidates for gene therapy as they readily transfect mammalian cells.

It will be appreciated that RNAi constructs directed to other complement components used in the formation of C5, C3, C5a, C3a, C5 convertase, and/or C3 convertase components can be used in accordance with the method described herein to reduce and/or inhibit interactions C5a and/or C3a with C5aR and C3aR in hematopoietic stem cells or bone marrow cells.

The RNAi constructs can include, for example, known Factor B, properdin, and Factor D siRNA that reduce expression of Factor B, properdin, and Factor D.

Moreover, it will be appreciated that other antibodies, small molecules, and/or peptides that reduce or inhibit the formation of C5, C3, C5a, C3a, C5 convertase, and/or C3 convertase and/or that reduce or inhibit interactions C5a and/or C3a with C5aR and C3aR in hematopoietic progenitor cells or osteoclast progenitor cells can be used as a complement antagonist in accordance with the method described herein. These other complement antagonists can be administered to the hematopoietic progenitor cells or osteoclast progenitor cells at amount to inhibit osteoclast differentiation.

Figure 2:
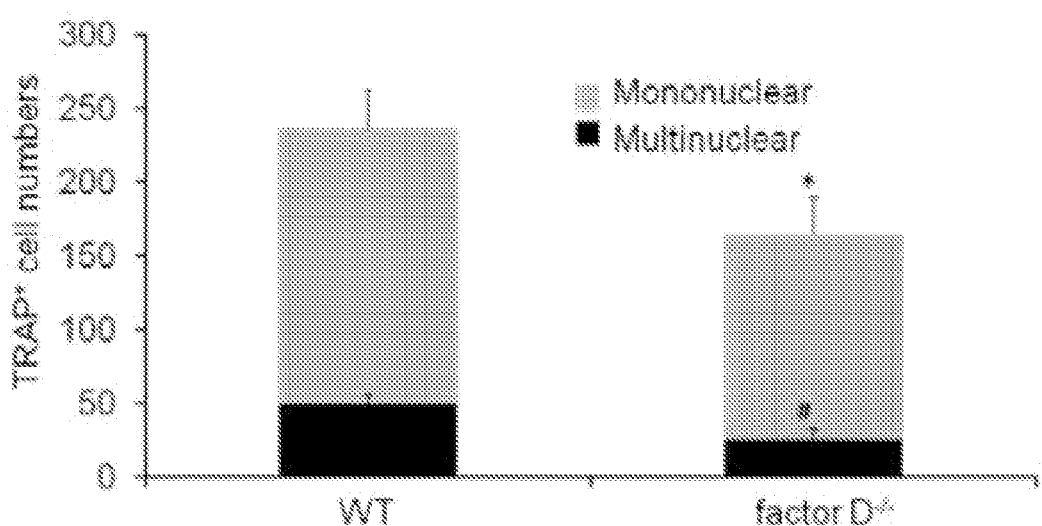
FIG. 2 illustrates a graph showing the number of TRAP$^+$ cells of WT and factor D$^{-/-}$ BM cells subjected to OC differentiation conditions.

Many complement antagonists are already in clinical trials for various human diseases, and one of them, an anti-C5 monoclonal antibody, has been approved by the FDA for the treatment of paroxysmal nocturnal hemoglobinuria (PNH), in which patients' erythrocytes are lysed by activated complement, leading to hemogloginuria and anemia. The C5aR antagonist JPE-1375 is a hexameric linear peptidomimetic molecule (M.W. 955) which has been shown to be effective in ameliorating disease symptoms in many mouse models where C5aR is integrally involved in the pathogenesis. JPE-1375 is reportedly more potent than another C5aR antagonist, PMX205, which has shown promising results in treating murine disease models such as amyotrophic lateral sclerosis and Alzheimer's disease. The Examples below show that the JPE-1375 antagonist inhibits mouse and human OC differentiation in vitro. The C3aR antagonist SB290157 is a synthesized small molecule which is commercially available from several companies including EMD Chemicals (Gibbstown, N.J.). It has been successfully used to treat murine models of neutrophilia, intestinal ischaemia/reperfusion injury and lupus nephritis. The Examples below demonstrate that these C3aR and C5aR antagonists significantly reduced TRAP$^+$ cells in human-derived bone marrow cells in vitro (FIG. 2). The C3aRA showed a significant decrease in both mono-nuclear and multi-nuclear TRAP$^+$ cells while C5aRA showed a decrease in both cell types, but only the mono-nuclear cells were at the level of statistical significance.

Examples of other complement antagonists include C5aR antagonists, such as AcPhe[Orn-Pro-D-cyclohexylalanine-Trp-Arg, prednisolone, and infliximab (Woodruff et al,. *The Journal of Immunology*, 2003, 171: 5514-5520), hexapeptide MeFKPdChaWr (March et al., *Mol Pharmacol* 65:868-879, 2004), PMX53, and N-[(4-dimethylaminophenyl)methyl]-N-(4-isopropylphenyl)-7-methoxy-1,2,3,4-tetrahydronaphthalen-1-carboxamide hydrochloride (W-54011) (Sumichika et al., J. Biol. Chem., Vol. 277, Issue 51, 49403-49407, Dec. 20, 2002), and a C3aR antagonist, such as SB 290157 (Ratajczak et al., Blood, 15 March 2004, Vol. 103, No. 6, pp. 2071-2078).

In other embodiments, the agent that inhibits C3aR and/or C5aR signaling in the hematopoietic progenitor cells or osteoclast progenitor cells, can include an IL-6/STAT3 signaling pathway antagonist that substantially decreases or inhibits the expression and/or functional activity of a component of the IL-6/STAT3 signaling pathway in the cell. The functional activity of the IL-6/STAT3 signaling pathway can be suppressed, inhibited, and/or blocked in several ways including: direct inhibition of the activity of IL-6 and/or STAT3 (e.g., by using neutralizing antibodies, small molecules or peptidomimetics, dominant negative polypeptides); inhibition of genes that express IL-6 and/or STAT-3 (e.g., by blocking the expression or activity of the genes and/or proteins); activation of genes and/or proteins that inhibit one or more of the functional activity of IL-6 and/or STAT3 (e.g., by increasing the expression or activity of the genes and/or proteins); inhibition of genes and/or proteins that are downstream mediators of the iNOS expression (e.g., by blocking the expression and/or activity of the mediator genes and/or proteins); introduction of genes and/or proteins that negatively regulate one or more of functional activity of IL-6 and/or STAT3 (e.g., by using recombinant gene expression vectors, recombinant viral vectors or recombinant polypeptides); or gene replacement with, for instance, a hypomorphic mutant of STAT-3 (e.g., by homologous recombination, overexpression using recombinant gene expression or viral vectors, or mutagenesis).

In an embodiment of the application, the IL-6/STAT3 signaling pathway antagonist is an IL-6 antagonist. In some aspects, the IL-6 antagonist can include a humanized IL-6 receptor-inhibiting monoclonal antibody. In certain aspects, the IL-6 antagonist is the product tocilizumab (a descriptive name sold under the trademark ACTEMRA by Roche, Switzerland). In other aspects, the IL-6 antagonist can include a vaccine that when administered to a subject generates IL-6 antibodies in the subject. An example of such a vaccine is disclosed in Fosergau et al. Journal of Endocrinology (2010) 204, 265-273.

In another embodiment, the IL-6/STAT3 signaling pathway antagonist is a tyrosine kinase inhibitor. Exemplary tyrosine kinase inhibitors for use in the present invention include but are not limited to tyrphostins, in particular AG-490, and inhibitors of Jak, Src, and BCR-Abl tyrosine kinases. Other tyrphostins suitable for use herein include, but are not limited to AG17, AG213 (RGS0864), AG18, AG82, AG494, AG825, AG879, AG1112, AG1296, AG1478, AG126, RG13022, RG14620, AG555, and related compounds. In certain aspects, a BCR-Abl tyrosine kinase inhibitor for use herein can include the product imatinib mesilate (a descriptive name sold under the trademark GLEEVEC® by Novartis, Switzerland).

In a further embodiment, the IL-6/STAT3 signaling pathway antagonist is an HMG CoA reductase inhibitor (3-hydroxymethylglutaryl coenzyme A reductase inhibitors) (e.g., statin). HMG-CoA (3-hydroxy methylglutaryl coenzyme A) reductase is the microsomal enzyme that catalyzes the rate limiting reaction in cholesterol biosynthesis (HMG-CoA Mevalonate.

Statins that can be used for administration, or co-administration with other agents described herein include, but are not limited to, simvastatin (U.S. Pat. No. 4,444,784), mevistatin, lovastatin (U.S. Pat. No. 4,231,938), pravastatin sodium (U.S. Pat. No. 4,346,227), fluvastatin (U.S. Pat. No. 4,739,073), atorvastatin (U.S. Pat. No. 5.273,995), cerivastatin, and numerous others described in U.S. Pat. Nos. 5,622,985, 5,135,935, 5,356,896, 4,920,109, 5,286,895, 5,262,435, 5,260,332, 5,317,031, 5,283,256, 5,256,689, 5,182,298, 5,369,125, 5,302,604, 5,166,171, 5,202,327, 5,276,021, 5,196,440, 5,091,386, 5,091,378, 4,904,646, 5,385,932, 5,250,435, 5,132,312, 5,130,306, 5,116,870, 5,112,857, 5,102,911, 5,098,931, 5,081,136, 5,025,000, 5,021,453, 5,017,716, 5,001,144, 5,001,128, 4,997,837, 4,996,234, 4,994,494, 4,992,429, 4,970,231, 4,968,693, 4,963,538, 4,957,940, 4,950,675, 4,946,864, 4,946,860, 4,940,800, 4,940,727, 4,939,143, 4,929,620, 4,923,861, 4,906,657, 4,906,624 and 4,897,402, the disclosures of which patents are incorporated herein by reference.

In yet another embodiment, the IL-6/STAT3 signaling pathway antagonist can be a STAT3 inhibitor. Examples of STAT3 inhibitors are described in U.S. Patent Application No. 2010/0041685 and can include 4-[3-(2,3-dihydro-1,4-benzodioxin-6-yl)-3-oxo-1-propen-1-yl]benzoic acid; 4{5-[(3-ethyl-4-oxo-2-thioxo-1,3-thiazolidin-5-ylidene)methyl]-2-furyl}benzoic acid; 4-[({3-[(carboxymethyl)thio]-4-hydroxy-l-naphthyl}amino) sulfonyl]benzoic acid; 3-({2-chloro-4-[(1,3-dioxo-1,3-dihydro-2H-inden-2-ylidene) methyl]-6-ethoxyphenoxy}methyl)benzoic acid; methyl 4-({ [3-(2-methoxy-2-oxoethyl)-4,8-dimethyl-2-oxo-2H-chromen-7-yl]oxy}met-hyl)benzoate; 4-chloro-3-{5-[(1,3-diethyl-4,6-dioxo-2-thioxotetrahydro-5(2H)-pyrimidinylidene)methyl]-2-furyl}benzoic acid; a functionally active derivative thereof and a mixture thereof. Other examples of STAT3 inhibitors are described in WO 2010/118309 and in G. Zinzalla et al. Bioorg. Med. Chem. Lett. 20 (2010)7029-7032.

The at least one agent that inhibits C3aR and/or C5aR signaling can be administered to the the hematopoietic progenitor cells or osteoclast progenitor cells in vivo or in vitro to inhibit osteoclast differentiation of the cells. The cells can be derived from a human subject, from a known cell line, or from some other source.

In some embodiments, the agent that inhibits at least one of C3aR and/or C5aR signaling in the hematopoietic progenitor cells or osteoclast progenitor cells may be used in a method for enhancing bone formation (i.e., increasing the amount of new bone that is laid down) and inhibiting bone resorption (i.e., reducing the amount of bone that is dissolved) simultaneously in a subject in need thereof by administering to the subject an agent described herein in an amount effective to enhance bone formation and inhibit bone resorption simultaneously in said subject. Nonlimiting examples of subjects for whom such treatment would be indicated and/or beneficial include women (e.g., postmenopausal; premenopausal) with osteoporosis or low bone mass, men with osteoporosis or low bone mass, subjects with a healing fracture, subjects undergoing prolonged immobilization, subjects who have been or are immobilized for a prolonged period, subjects likely to undergo or experience prolonged immobilization, subjects with estrogen deficiency, etc., as would be known in the art.

Also provided herein is a method for inducing deposition and maturation of bone in a subject in need thereof (e.g., a subject having a compromised bone condition) by administering to the subject an agent described herein in an amount effective to induce deposition and maturation of bone in the subject. In some embodiments, a compromised bone condition is at a targeted site of the subject. The site may be an intervertebral space, a facet joint, a site of a bone fracture, bones of the mouth, chin and jaw, or an implant site.

Also provided herein is a method for improving bone marrow reconstitution in a subject in need thereof by administering to the subject an agent that inhibits at least one of C3aR and/or C5aR signaling in an amount effective to improve bone marrow reconstitution (i.e., restoring (e.g., partially or fully) of bone marrow cells in a subject, which can be, for example, a subject having chemotherapy, radiation or other treatments that deplete bone marrow cells. For example, a subject undergoing chemotherapy with or without radiation would benefit from more rapid restoration of cells in the bone marrow in order to prevent opportunistic infections. A subject of these methods can also be a subject having or suspected of having a hematologic disorder (e.g., aplastic anemia; myelodysplasia) that depletes bone marrow cells. Such an improvement or enhancement or increase in bone marrow reconstitution is in comparison to a subject to whom the agent that inhibits at least one of C3aR and/or C5aR signaling has not been administered.

In some embodiments, the methods described herein can be employed in methods of ex vivo expansion of stem cells, such as hematopoietic stem cells, carried out according to protocols known in the art. Thus, a method of expanding stem cells ex vivo, comprising contacting the agent that inhibits at least one of C3aR and/or C5aR signaling with stem cells from a subject, wherein said stem cells are maintained under conditions whereby they are reintroduced into the subject.

For example in some ex vivo embodiments, the stem cells are obtained from a subject, e.g., a human, e.g., from peripheral blood, umbilical cord blood, or bone marrow, and the stem cells are contacted with the agent that inhibits at least one of C3aR and/or C5aR signaling outside the body of the subject. Ex vivo embodiments include obtaining stem cells, such as hematopoietic stem cells, from a subject and culturing the cells for a period of time prior to use (e.g., for transplantation). In some embodiments, after contact with the agent that inhibits at least one of C3aR and/or C5aR signaling, the cells are delivered to a subject, e.g., the same subject from which the cells were isolated (autologous donation) or a different subject (non-autologous (e.g., syngeneic or allogeneic) donation).

Nonlimiting examples of a subject for whom these methods would be indicated or beneficial include a subject having or who has had chemotherapy, a subject having or who has had radiation, a subject having aplastic anemia, a subject having myelodysplasia, and any combination thereof.

Administration of the agent that inhibits at least one of C3aR and/or C5aR signaling in the hematopoietic progenitor cells or osteoclast progenitor cells can be by any suitable route, including intrathecal injection, subcutaneous, cutaneous, oral, intravenous, intraperitoneal, intramuscular injection, in an implant, in a matrix, in a gel, or any combination thereof.

A bone condition that can be treated according to the methods described herein may be one or more of broken bones, bone defects, bone transplant, bone grafts, bone cancer, joint replacements, joint repair, fusion, facet repair, bone degeneration, dental implants and repair, bone marrow deficits and other conditions associated with bone and boney tissue. Bone defects may be a gap, deformation and/or a nonunion fracture in a bone.

Bone degeneration may be due to osteopenia or osteoporosis (e.g., the patient is afflicted with geriatric or senile osteoporosis, with post-menopausal osteoporosis, etc.), or due to dwarfism.

Joint replacements that may be treated include vertebral, knee, hip, tarsal, phalangeal, elbow, ankle and/or other articulating joints or replacements thereof. Joint repairs include, but are not limited to, vertebral, knee, hip, tarsal, phalangeal, elbow, ankle, and sacroiliac joint repairs.

In designing appropriate doses of the agents that inhibit at least one of C3aR and/or C5aR signaling for the treatment of bone conditions, one may readily extrapolate from the knowledge in the literature in order to arrive at appropriate doses for clinical administration. To achieve a conversion from animal to human doses, one would account for the mass of the agents administered per unit mass of the experimental animal and, preferably, account for the differences in the body surface area (m2) between the experimental animal and the human patient. All such calculations are well known and routine to those of ordinary skill in the art.

It will be understood that lower doses may be more appropriate in combination with other agents, and that high doses can still be tolerated.

In some embodiments, the agent that inhibits at least one of C3aR and/or C5aR signaling can be administered directly to or about the periphery of the bone condition being treated to inhibit osteoclast differentiation. In one aspect of the invention, the agent the agent that inhibits at least one of C3aR and/or C5aR signaling can be delivered to or about the periphery of the site of the bone condition being treated by administering the agent neat or in a pharmaceutical composition to or about the bone. The pharmaceutical composition can provide localized release of the agent to the bone marrow or bone marrow cells being treated. Pharmaceutical compositions will generally include an amount of the agent the agent that inhibits at least one of C3aR and/or C5aR signaling admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. Moreover, for human administration, preparations should meet sterility, pyrogenicity, general safety and purity standards as required by FDA Office of Biological Standards.

The pharmaceutical composition can be in a unit dosage injectable form (e.g., solution, suspension, and/or emulsion). Examples of pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (e.g., glycerol, propylene glycol, liquid polyethylene glycol, and the like), suitable mixtures thereof and vegetable oils.

Proper fluidity can be maintained, for example, by the use of a coating, such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various amounts of the other ingredients, as desired.

Pharmaceutical "slow release" capsules or "sustained release" compositions or preparations may be used and are generally applicable. Slow release formulations are generally designed to give a constant drug level over an extended period and may be used to deliver the agent. The slow release formulations are typically implanted in the vicinity of the bone condition, for example, at the site of the bone condition (e.g., bone marrow).

Examples of sustained-release preparations include semipermeable matrices of solid hydrophobic polymers containing the agent that inhibits at least one of C3aR and/or C5aR signaling, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773,919; copolymers of L-glutamic acid and γethyl-L-glutamate; non-degradable ethylene-vinyl acetate; degradable lactic acid-glycolic acid copolymers, such as the LUPRON DEPOT (injectable microspheres composed of lactic acid-glycolic acid copolymer and leuprolide acetate); and poly-D-(−)-3-hydroxybutyric acid.

While polymers such as ethylene-vinyl acetate and lactic acid-glycolic acid enable release of molecules for over 100 days, certain hydrogels release proteins for shorter time periods. When encapsulated agent remain in the body for a long time, and may denature or aggregate as a result of exposure to moisture at 37° C., thus reducing biological activity and/or changing immunogenicity. Rational strategies are available for stabilization depending on the mechanism involved. For example, if the aggregation mechanism involves intermolecular S—S bond formation through thio-disulfide interchange, stabilization is achieved by modifying sulfhydryl residues, lyophilizing from acidic solutions, controlling moisture content, using appropriate additives, developing specific polymer matrix compositions, and the like.

In certain embodiments, liposomes and/or nanoparticles may also be employed with the agent that inhibits at least one of C3aR and/or C5aR signaling. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Phospholipids can form a variety of structures other than liposomes when dispersed in water, depending on the molar ratio of lipid to water. At low ratios, the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made.

In another aspect, the agent that inhibits at least one of C3aR and/or C5aR signaling can be administered directly to or about the periphery of the bone condition being treated by introducing an agent into target cells, such as bone marrow cells or the hematopoietic progenitor cells or osteoclast progenitor cells, that causes, increases, and/or upregulates expression of at least one of C3, C5, C3a, C5a, a C3aR agonist, or C5aR agonist in or about the periphery of the bone marrow cells or the hematopoietic progenitor cells or osteoclast progenitor cells. The at least one of at least one of C3, C5, C3a, C5a, a C3aR agonist, or C5aR agonist expressed in or about the periphery of the bone condition can be an expression product of a genetically modified cell. The target cells can include cells within or about the periphery of the bone condition or ex vivo cells that are biocompatible with the bone condition being treated. The biocompatible cells can also include autologous cells that are harvested from the subject being treated and/or biocompatible allogeneic or syngeneic cells, such as autologous, allogeneic, or syngeneic stem cells (e.g., mesenchymal stem cells), progenitor cells (e.g., multipotent adult progenitor cells) and/or other cells that are further differentiated and are biocompatible with the bone condition being treated.

In other embodiments of the application, osteoblast differentiaion can be promoted or stimulated by administering to stromal cells, mesenchymal stem cell (MSC), MAPC, induced pluripotent stem cell (IPC), or osteoblast progenitor cells an agent that promotes or stimulates C3aR and/or C5aR signaling of the cells. The agent can be selected from the group consisting of C3, C5, C3a, C5a, a C3aR agonist, a C5aR agonist, a DAF antagonist, or combination thereof. Promotion or stimulation of C3aR and/or C5aR activation in to a stromal cells, MSCs, MAPCs, IPCs, and osteoblast progenitor cells can induce osteoblast differentiation and promote bone regeneration.

The MSCs can include the formative pluripotent blast or embryonic cells that differentiate into the specific types of connective tissues, (i.e., the tissue of the body that support specialized elements, particularly including adipose, osseous, cartilaginous, elastic, muscular, and fibrous connective tissues depending on various in vivo or in vitro environmental influences). These cells are present in bone marrow, blood, dermis, and periosteum and can be isolated and purified using various well known methods, such as those methods disclosed in U.S. Pat. No. 5,197,985 to Caplan and Haynesworth, herein incorporated by reference, as well as other numerous literature references.

The MAPCs in accordance can include adult progenitor or stem cells that are capable of differentiating into cells types beyond those of the tissues in which they normally reside (i.e., exhibit plasticity). MAPCs express the ES cell—specific transcription factor Oct3/4 (POU5F1) but not Nanog. FACS analysis demonstrates that MAPCs do not express class I and II MHC, CD34, CD44, CD45 and are CD105 (also endoglin, or SH2) negative. Hence, MAPCs differ from classical MSCs that are Oct4 low/negative but CD44 and MHC class I positive and differentiate essentially into mesodermal cells but not cells of endoderm and ectoderm. Compared with mesoangioblasts, MAPCs do not express CD34 and Flkl (KDR), and have a broader differentiation ability. MAPCs differ from hematopoietic stem cells (HSC) in that MAPCs do not express CD45, CD34, and cKit, but like HSC, MAPC express Thyl, AC133 (human MAPC) and Scal (mouse) albeit at low levels. In the mouse, MAPC express low levels of stage specific embryonic antigen (SSEA)-1, and express low levels of the transcription factors Oct4 and Rex1, known to be important for maintaining embryonic stem (ES) cells undifferentiated and to be down-regulated when ES cells undergo somatic cell commitment and differentiation.

MAPCs can be cultured from mouse brain and mouse muscle. Of note, the differentiation potential and expressed gene profile of MAPC sderived from the different tissues appears to be highly similar. Unlike most adult somatic stem cells, MAPC proliferate without obvious signs of senescence, and have active telomerase. Human, mouse and rat MAPCs have been shown to be successfully differentiated into typical mesenchymal lineage cells, including osteoblasts, chondroblasts, adipocytes and skeletal myoblasts. In addition, human, mouse and rat MAPCs can be induced to differentiate into cells with morphological, phenotypic and functional characteristics of endothelial cells, and morphological, phenotypic and functional characteristics of hepatocytes.

An enriched population of iPCs can formed as described by known methods described in, for example, Mali P, Ye Z, Hommond HH, Yu X, Lin J, Chen G, Zou J, Cheng L. Stem Cells. 2008 August; 26(8):1; Stadtfeld M, Nagaya M, Utikal J, Weir G, Hochedlinger K. Science. 2008 Nov 7;322(5903): 945-9; and Park I H, Lerou P H, Zhao R, Huo H, Daley G Q. *Nat Protoc.* 2008; 3(7):1180-6.

In some embodiments, an enriched population of MSCs can be prepared by isolating bone marrow cells from the femurs of a subject. Cells can then be separated by Percoll density gradient. The cells can be centrifuged and washed with PBS supplemented with penicillin, and streptomycin (Invitrogen, Carlsbad, Calif.). The cells can then be re-suspended and plated in DMEM-LG (GIBCO, Invitrogen, Carlsbad, Calif.) with 10% FBS and 1% antibiotic and antimycotic (GIBCO, Invitrogen, Carlsbad, Calif.) and maintained at 37° C. Non-adherent cells can then be removed by replacing the medium after 3 days. At this point, adherent cells can then ber detached by incubation with 0.05% trypsin and 2 mM EDTA (Invitrogen, Carlsbad, Calif.) for 5 minutes and subsequently re-plated.

To prevent non-specific selection of monocytes and macrophages, MSCs Cultures can be immunodepleted of CD45+, CD34+ cells by negative selection using primary PE-conjugated mouse anti-rat CD45 (BD Biosciences, San Diego, Calif.) and CD34 antibodies (Santa Cruz Biotechnology, Inc., Santa Cruz, Calif.) using the EasySep PE selection kit according to the manufacturer's instruction (Stem Cell technologies). The MSCs can then tested by FACS and were positive for CD90, CD29 and negative for CD34 and CD45. The multipotentiality of resulting cells can be subsequently verified with the use of in vitro assays to differentiate MSCs into osteogenic (alkaline phosphatase activity), adipogenic (oil red 0 staining) and chondrogenic (Alcian Blue) lineages according to published protocols.

In some embodiments, the stromal cells, MSCs, MAPCs, IPCs, or osteoblast progenitor cells treated with an agent that promotes or stimulates C3aR and/or C5aR signaling of the cells can be provided in and/or on a substrate, solid support, and/or wound dressing for cells to a muscloskeletal injury site. As used herein, the term "substrate," or "solid support" and "wound dressing" refer broadly to any substrate when prepared for, and applied to, a wound for protection, absorbance, drainage, etc. The substrate one of the numerous types of substrates and/or backings that are commercially available, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (non-woven composites of fibers from calcium alginate), and cellophane (cellulose with a plasticizer).

In one example, the substrate can be a bioresorbable implant that includes a polymeric matrix and the stromal cells, MSCs, MAPCs, IPCs, or osteoblast progenitor cells treated with an agent that promotes or stimulates C3aR and/or C5aR signaling of the cells dispersed in the matrix. The polymeric matrix may be in the form of a membrane, sponge, gel, or any other desirable configuration. The polymeric matrix can be formed from biodegradable polymer. It will be appreciated, however, that the polymeric matrix may additionally comprise an inorganic or organic composite. The polymeric matrix can comprise anyone or combination of known materials including, for example, chitosan, poly(ethylene oxide), poly (lactic acid), poly(acrylic acid), poly(vinyl alcohol), poly(urethane), poly(N-isopropyl acrylamide), poly (vinyl pyrrolidone) (PVP), poly (methacrylic acid), poly(p-styrene carboxylic acid), poly(p-styrenesulfonic acid), poly (vinylsulfonicacid), poly(ethyleneimine), poly(vinylamine), poly(anhydride), poly(Llysine), poly(L-glutamic acid), poly (gamma-glutamic acid), poly(carprolactone), polylactide, poly(ethylene), poly(propylene), poly(glycolide), poly(lactide-co-glycolide), poly(amide), poly(hydroxylacid), poly (sulfone), poly(amine), poly(saccharide), poly(HEMA), poly (anhydride), collagen, gelatin, glycosaminoglycans (GAG), poly (hyaluronic acid), poly(sodium alginate), alginate, hyaluronan, agarose, polyhydroxybutyrate (PHB), and the like.

It will be appreciated that one having ordinary skill in the art may create a polymeric matrix of any desirable configuration, structure, or density. By varying polymer concentration, solvent concentration, heating temperature, reaction time, and other parameters, for example, one having ordinary skill in the art can create a polymeric matrix with any desired physical characteristic(s). For example, the polymeric matrix may be formed into a sponge-like structure of various densities. The polymeric matrix may also be formed into a membrane or sheet, which could then be wrapped around or otherwise shaped to a wound. The polymeric matrix may also be configured as a gel, mesh, plate, screw, plug, or rod. Any conceivable shape or form of the polymeric matrix is within the scope of the present invention. In an example of the present invention, the polymeric matrix can comprise an osteoconductive matrix.

In other aspects, the polymer matrix seeded the stromal cells, MSCs, MAPCs, IPCs, or osteoblast progenitor cells treated with an agent that promotes or stimulates C3aR and/or C5aR signaling of the cells can comprise bone graft or bone graft substitute. In some embodiments, an osteoconductive matrix can be used to support the mammalian cells and include collagen fibers coated with hydroyapatite. In other aspects, the osteoconductive matrix is saturated with the population of the cells. In one particular example, the stromal cells, MSCs, MAPCs, IPCs, or osteoblast progenitor cells treated with an agent that promotes or stimulates C3aR and/or C5aR signaling of the cells is delivered to the musculoskeletal injury or to an area proximate the skeletal injury. The seeded osteoconductive matrix may then be implanted adjacent to a bone fracture site for the treatment of a skeletal injury in a subject.

In another aspect of the application, a therapeutic composition can include a bone graft, such as an autograft, that seeded with the stromal cells, MSCs, MAPCs, IPCs, or osteoblast progenitor cells treated with an agent that promotes or stimulates C3aR and/or C5aR signaling of the cells. Bone grafting is commonly used to repair fractured bones. While grafting can include artificial bone replacement, autografting is often the most successful type of grafting available. Bones tend to more readily adhere to one another when a subject's own bone is used. The most common donor area is the iliac crest, which is located in the subject's pelvis.

A bone graft may also include an allograft bone graft. Typically, an allograft bone graft is bone obtained from cadavers. An allograft may be sterilized and/or fresh frozen or freeze-dried prior to grafting. An allograft may also be used as a bone graft supplement (to the subject's own bone) in subjects.

In a further aspect, the stromal cells, MSCs, MAPCs, IPCs, or osteoblast progenitor cells treated with an agent that promotes or stimulates C3aR and/or C5aR signaling of the cells can be provided in or on a surface of a medical device used to treat a musculoskeletal injury. The medical device can comprise any instrument, implement, machine, contrivance, implant, or other similar or related article, including a component or part, or accessory which is recognized in the official U.S. National Formulary, the U.S. Pharmacopoeia, or any supplement thereof; is intended for use in the diagnosis of disease or other conditions, or in the cure, mitigation, treatment, or prevention of disease, in humans or in other animals; or, is intended to affect the structure or any function of the body of humans or other animals, and which does not achieve any of its primary intended purposes through chemical action within or on the body of man or other animals, and which is not dependent upon being metabolized for the achievement of any of its primary intended purposes.

The invention will be further described in the following examples, which do not limit the scope of the invention described in the claims.

EXAMPLE 1

In this Example, using knockout mice deficient of C3, factor D, C3aR, and/or C5aR, we show the role of complement in $1.25(OH)_2$ vitamin $D_3$—induced OC differentiation. We found that BM cells from $C3^{-/-}$ mice generated significantly decreased numbers of OC after stimulation. In accordance with these results, $C3^{-/-}$ BM cells exhibited reduced receptor activator of nuclear factor kB ligand (RANKL)/osteoprotegerin (OPG) expression ratios and produced decreased amounts of macrophage colonystimulating factor (M-CSF) and IL-6 during OC differentiation. More importantly, we also found that in addition to C3, BM cells locally produce factor B, factor D, and C5 after $1.25(OH)_2$ vitamin $D_3$ stimulation, and that the alternative pathway of complement activation is required to activate C3 for efficient OC differentiation. In addition to the C3 receptors reported before, our data show that C3aR/ C5aR are also integrally involved in OC differentiation, and their regulatory roles are mediated, at least in part, through modulating local IL-6 production.

Methods

Genetically Engineered Mice

Wild-type (WT) C57BL/6 and $C3^{-/-}$ mice were ordered from The Jackson Laboratory. Factor $D^{-/-}$ mice were gifts from Dr Yuanyuan Ma (University of Alabama at Birmingham), and factor $B^{-/-}$ mice were kindly provided by Dr Michael Holers (University of Colorado at Denver). $C3aR^{-/-}$ and $C5aR^{-/-}$ mice were generously provided by Dr Craig Gerard (Harvard University), and $C3aR^{-/-}C5aR^{-/-}$ mice were identified by polymerase chain reaction (PCR) genotyping after crossing the $C3aR^{-/-}$ with $C5aR^{-/-}$ mice. All mice are on the C57BL/6 background, and all animal studies were performed under an approved protocol in accordance with the guidelines of the Institutional Animal Care and Use Committee of Case Western Reserve University.

BM-Cell Cultures

Human BM cells from healthy donors were obtained from the Hematopoietic Stem Cell Core Facility of Case Western Reserve University. Murine BM cells were isolated from 8- to 12-week-old female mouse femurs and tibias, washed, and collected in 15-mL tubes in α-modified Eagle medium (MEM) containing 10% fetal bovine serum (FBS) that was heat-inactivated to eliminate complement activity. For OC differentiation, $2\times10^6$ BM cells were cultured in complete α-MEM medium in wells of a 24-well plate together with $1\times10^{-8}$M $1.25(OH)_2$ vitamin $D_3$ (Cayman Chemical) as described before. Cultures were fed every 3 days with fresh media. For IL-6 or C5aR antagonist (C5aRA)/C3aR antagonist (C3aRA) supplementation experiments, 20 ng/mL IL-6 (R&D Systems) or 50 µM of each antagonist or both (C5aRA: JPE-1375; custom synthesized by Anaspec; C3aRA: SB290157; purchased from BMD Chemicals) were included in the medium. For C3a and/or C5a supplementation experiments, 50 ng/mL purified C3a (BD Biosciences) or C5a (Cell Sciences) or both were added daily into WT and $C3^{-/-}$ BM-cell cultures. To neutralize IL-6 in samples treated with C3a/C5a, 10 ng/mL rat anti-IL-6 mAb (Clone 6B4 IGH 54; eBioscience) were added every 2 days. At day 12, differentiated OCs were identified by conventional tartrate-resistant acid phosphatase (TRAP) staining using a kit (Sigma-Aldrich) and following the protocol provided by the manufacturer. Total numbers of TRAP-positive cells in each well were counted under a microscope, and cells containing 3 or more nuclei were categorized as multinucleated.

Primary Calvarial Osteoblast and Splenocyte Cocultures

Primary calvarial osteoblasts (OBs) were isolated from newborn WT and $C3^{-/-}$ mice, following protocols. In brief, dissected calvariae from 2- to 3-day-old WT and $C3^{-/-}$ mice were digested with 1 mg/mL collagenase D (Roche) and 0.05% trypsin (Invitrogen) in Hanks buffered salt solution. Cells from second and third digestions were pooled and grown in α-MEM with antibiotics and 10% FBS. At confluence, cells were trypsinized and counted for coculture experiments. To set up coculture experiments, $2\times10^4$ primary calvarial OBs from WT or $C3^{-/-}$ mice were cultured with $2\times10^6$ splenocytes from WT and $C3^{-/-}$ mice together with $1\times10^{-8}$ $1.25(OH)_2$ vitamin $D_3$. The resultant TRAP-positive cells were counted after 12 days of coculture.

Complement Assays

To determine that functional factor B, factor D, and C5 are produced during OC differentiation, culture supernatants were collected at day 6 from $2\times10^6$ WT BM cells stimulated with $1\times10^{-8}$M $1.25(OH)_2$ vitamin $D_3$ and assayed for complement activities. For functional factor B and D detection, collected culture supernatants were directly added into zymosan C3 uptake assays with factor B or D deficient mouse sera. In brief, sera were prepared by bleeding male WT, factor $B^{-/-}$, or factor $D^{-/-}$ mice through the tail vein. After this, 20% BM cell-conditioned culture supernatants or control media were added into 10% of WT, factor $B^{-/-}$, or factor $D^{-/-}$ serum together with 30 µg/mL zymosan (Sigma-Aldrich) in gelatin veronal buffer (GVB)/Mg$^2$tEGTA(ethylene glycol tetraacetic acid) buffer and incubated at 37° C. for 30 minutes. After washing, C3b deposition was assessed by fluorescein isothiocyanate (FITC)—anti-mouse C3 mAb (Cedarlane) staining, followed by flow cytometry analysis. For functional C5 detection, BM cell-culture supernatant or control media was concentrated 10-fold using a Microcon (Millipore) and added into E$^{sha}$-based hemolytic assays using 10% of human C5-depleted serum (Complement Tech). The ability of the BM cell—conditioned media to compensate the C5 deficiency in the serum was assessed by measuring $OD_{541}$ to quantify C5b-9 (membrane attack complex)—mediated sheep erythrocyte hemolysis.

IL-6 and M-CSF ELISA

For IL-6—level measurements, culture supernatants were collected at day 12 after 1.25(OH)$_2$ vitamin D3 stimulation, and standard IL-6 enzymelinked immunosorbent assay (ELISA; R&D Systems) was used according to the protocol provided by the manufacturer. For M-CSF assays, culture supernatants were collected at day 3 after stimulation, concentrated by ultrafiltration using a centrifugal concentrator (molecular weight [MW] cutoff: 3000; Millipore), then analyzed by a murine M-CSF ELISA kit (PeproTech), following the manufacturer-provided protocol.

Assessment of RANKL/OPG Expression Ratios

To compare RANKL/OPG expression levels in WT and C3$^{-/-}$ BM cells during OC differentiation, $2 \times 10^6$ BM cells were isolated from WT or C3$^{-/-}$ mice and cultured in complete α-MEM with and without the presence of $1 \times 10^{-8}$M 1.25(OH)$_2$ vitamin D$_3$. At 24 hours, total RNA was purified from the cells using TRIzol (Invitrogen), and reverse transcribed using a first-strand cDNA synthesis kit (Invitrogen), following protocols provided by the manufacturer. The relative expression levels of RANKL and OPG were assessed by SYBR Green-based quantitative reverse transcription (RT)—PCR (qRT-PCR; GoTag qPCR master mix; Promega). In brief, the qRT-PCR was carried out in triplicate for RANKL, OPG, and β-actin (internal control) of each sample on an ABI PRISM 7500 machine (Applied Biosystems). The data were analyzed and normalized against levels of RANKL and OPG in BM cells without 1.25(OH)$_2$ vitamin D$_3$ stimulation by the 7500 SDS Version 1.3 software package (Applied Biosystems). Dissociation experiments were used to ensure that the fluorescent signal for each amplicon was derived from the PCR products only.

Results

C3$^{-/-}$ BM Cells Generate Fewer OCs than WT BM Cells

To examine whether the absence of locally produced C3 from BM cells will inhibit OC generation we incubated WT and C3$^{-/-}$ BM cells with 1.25(OH)$_2$ vitamin D$_3$ and compared the number of TRAP-positive cells on day 12. As shown in FIG. 3, after stimulation, C3$^{-/-}$ BM cells produced 119±31 TRAP-positive mononuclear cells and 21±6 multinucleated TRAP-positive cells per well, while WT BM cells generated 230±26 TRAP-positive mononuclear cells and 49±10 multinucleated TRAP-positive cells (P<0.05). These results indicate that the absence of C3 from BM cells reduces 1.25(OH)$_2$ vitamin D$_3$-stimulated OC differentiation by nearly 50%.

C3$^{-/-}$ BM cells Produced Reduced Levels of M-CSF and Failed to Efficiently Up-regulate RANKL Expression after 1.25(OH)2 Vitamin D3 Stimulation We next assessed the levels of M-CSF in WT and C3$^{-/-}$ BM cell-culture supernatants using a standard ELISA kit. These assays showed that, compared with 23.7±2.1 pg/mL M-CSF in WT BM cell-conditioned media, C3$^{-/-}$ BM cell—conditioned media contained only 10.9±1.2 pg/mL of M-CSF (FIG. 4A). Because of the well-established roles of RANKL and OPG in osteoclast generation, we also analyzed the expression levels of RANKL and OPG in WT and C3$^{-/-}$ BM cells after 1.25(OH)$_2$ vitamin D$_3$ stimulation by qRT-PCR. Consistent with previous reports by others, in WT BM cells, 1.25(OH)$_2$ vitamin D$_3$ stimulation markedly up-regulated RANKL expression (~6-fold), but had little effect on OPG expression (FIG. 4B). However, the same assays demonstrated that C3$^{-/-}$ BM cells failed to significantly up-regulate RANKL expression (1.6-fold), and that the expression levels of OPG remained essentially unchanged. These results indicate that during OC differentiation, C3$^{-/-}$ BM cells produced decreased levels of M-CSF and decreased RANKAL/OPG ratios, which is in accordance with the lower numbers of OCs generated.

BM Cells Locally Produce Functional Factor B, Factor D, and C5 in Addition to C3 During Differentiation For C3 to impact any cell, it first needs to be activated. To examine how BM cell-generated C3 could be activated to regulate OC differentiation, we assessed the presence of factor B and factor D, components essential for the activation of C3 through the alternative pathway of complement activation, as well as C5, the component required for C5a generation. The presence of mRNA for factor B, factor D, and C5 were first confirmed by RT-PCR (data not shown), and then the presence of complement proteins were tested with functional assays of the BM cell-conditioned media using sera deficient of factor B, factor D, or C5. These assays (FIG. 5) showed that after 1,25(OH)$_2$ vitamin D$_3$ stimulation, BM cell-conditioned media compensated the absence of factor B, factor D, or C5 (FIG. 5) in zymosanbased C3b uptake and E$^{shA}$-based hemolytic assays, indicating that BM cells produce functional factor B, factor D, and C5 during differentiation. These results indicate that C3 could be activated through the alternative pathway during BM cell differentiation, leading to the production of complement activation products, including ligands for C3 receptors and the released anaphylatoxins, C3a/C5a.

Alternative Pathway of Complement Activation is Required for Efficient OC Differentiation To determine whether the alternative pathway of complement activation is required to activate the C3 locally produced by the BM cells, and thus implicating complement activation in the regulation of OC differentiation, we compared the numbers of OCs generated from WT and factor D$^{-/-}$ BM cells after 1.25(OH)$_2$ vitamin D$_3$ stimulation. Factor D is essential for the alternative pathway of complement activation. These osteoclast assays (FIG. 6) showed that factor D$^{-/-}$ BM cells generated 163±16 mononuclear and 25±8 multinucleated TRAP-positive cells per well, compared with 236±16 mononuclear and 50±2 multinucleated TRAP-positive cells in wells containing WT BM cells (P<0.05). These results indicate that the alternative pathway of complement activation is required to activate C3 for efficient OC differentiation from BM cells after 1.25(OH)$_2$ vitamin D$_3$ stimulation.

C3aR and C5aR are Required for Efficient OC Differentiation

Since BM cells locally produce both C3 and C5 during OC differentiation, and their activation through the alternative pathway can generate C3a and C5a, we next examined whether the receptors for these ligands, C3aR and C5aR, could regulate OC differentiation. We isolated BM cells from WT, C3aR$^{-/-}$, C5aR$^{-/-}$, and C3aR$^{-/-}$C5aR$^{-/-}$ mice, then incubated them with 1.25(OH)$_2$ vitamin D$_3$, following the same OC differentiation protocol. The osteoclast induction assays (FIG. 7A) demonstrated that, compared with WT BM cells (226±22 mononuclear and 55±5 multinucleated cells), C3aR$^{-/-}$ and C5aR$^{-/-}$ BM cells generated a reduced number of TRAP-positive cells; C3aR$^{-/-}$ BM cells had 115±12 mononuclear and 20±3 multinucleated cells, and C5aR$^{-/-}$ BM cells had 164±6 mononuclear and 40±5 multinucleated cells, while the double-knockout C3aR$^{-/-}$C5aR$^{-/-}$ BM cells had the least number of TRAP-positive cells (91±10 mononuclear and 20±7 multinuclear cells). In complementary experiments, during 1.25(OH)$_2$ vitamin D$_3$ stimulation, we treated WT BM cells with C3aRA(SB290157), C5aRA(JPE-1375), or both. In these assays (FIG. 7B), compared with the placebo (217±25 mononuclear and 42±9 multinuclear cells), C3aRA significantly inhibited OC generation (156±23 mononuclear and 29±7 multinuclear cells). While C5aRA appeared to reduce numbers of both mono- and multinucleated TRAP-positive cells (176±29 mononuclear and 34±8 multinuclear cells), it did not reach a statistical significance (P=0.068 for mononuclear cells and P=0.12 for multinucleated cells). However, a combination of C3aRA and C5aRA inhibited OC generation synergistically (66±4 mononuclear and 16±2 multinuclear cells; P<0.05). These results indicate that in addition to C3 receptors, C3aR and, possibly, C5aR are also required for efficient OC generation, in which C3aR may play a more prominent role than C5aR.

C3aR/C5aR Regulated IL-6 Expression is Involved in OC Differentiation

We next explored a potential mechanism underlying the C3aR/C5aR-mediated effects on OC differentiation, which is based on previous reports that IL-6 augments OC generation, and that C3aR/C5aR stimulates IL-6 production in many types of cells. We measured IL-6 levels by ELISA in WT, C3$^{-/-}$, and C3aR$^{-/-}$C5aR$^{-/-}$ BM cell-conditioned media after 1.25(OH)$_2$ vitamin D$_3$ stimulation. These measurements showed that, compared with 357.5±66.4 pg/mL IL-6 in WT BM cell-conditioned media, there was only 72.8±12.7 or 86.2±16.3 pg/mL IL-6 in C3$^{-/-}$ or C3aR$^{-/-}$ C5aR$^{-/-}$ BMcell-conditioned media (FIG. 8A).

To causally link reduced levels of IL-6 to decreased OC differentiation in C3$^{-/-}$ BM cells, we repeated the differentiation experiments with WT and C3$^{-/-}$ BM cells and, this time, supplemented 20 ng/mL of IL-6 into the C3$^{-/-}$ BM cell-culture daily and counted TRAP-positive cells at 12 days. As shown in FIG. 8B, supplementation of exogenous IL-6 into C3$^{-/-}$ BM cell cultures increased the numbers of TRAP-positive cells from 108±17 (mononuclear) and 31±4 (multinucleated) to 249±39 (mononuclear) and 52±9 (multinucleated) (P<0.05), suggesting that complement regulates OC differentiation, at least in part, through modulating local IL-6 production.

To further verify that C3aR/C5aR are integrally involved in OC differentiation, and IL-6 is the underlying mechanism, we next incubated WT or C3$^{-/-}$ BM cells with purified C3a, C5a, or both during the differentiation process, and neutralized IL-6 using an anti-IL-6 mAb in the cultures stimulated with C3a/C5a. These assays showed that while exogenous C3a increased the numbers of resultant OC from both WT and C3$^{-/-}$ BM cells, C5a did not appear to have a significant effect on TRAP$^+$ cell formation (FIG. 8C-D). Neutralizing IL-6 totally ablated the effects of C3a/C5a on augmenting OC generation from both the WT and C3$^{-/-}$ BM cells. Interestingly, exogenous C3a and the combination of C3a/C5a appeared to have a greater effect on C3$^{-/-}$ BM cells than WT BM cells (66.7% increase vs. 36.2% increase of mononuclear cells and 87.5% increase vs. 33.3% increase of multinucleated cells), possibly due to the lack of endogenous C3a/C5a production in C3$^{-/-}$ BM cells, while WT BM cells can still make the baseline of C3a/C5a during differentiation. Similarly, neutralization of IL-6 after C3a/C5a treatment in WT BM cells reduced OC numbers below placebo-treated WT BM cells, while neutralizing IL-6 in C3$^{-/-}$ BM cells just ablated C3a/C5a effects without further reducing OC numbers below the baseline, which is consistent with previous reports by others that IL-6 is critical in OC differentiation, and our findings that C3$^{-/-}$ BM cells only produce trace amount of IL-6 during OC differentiation.

Locally Produced Complement also Regulates OC Differentiation in Humans

To determine whether the above-observed results would apply to humans, we subjected normal human BM cells to OC differentiation conditions with and without the C3aR/C5aR antagonists, then analyzed the conditioned media for the presence of factor B, factor D, and C5, and quantified the resultant TRAP$^+$ cells. These assays showed that, like the results with the mouse system, human BM cells locally produce functional factor B, factor D, and C5 (FIG. 9A) during OC differentiation, and that blocking C3aR and/or C5aR significantly inhibited OC generation (FIG. 9B).

EXAMPLE 2

Direct Complement Effects On OC Differentiation

To maintain bone homeostasis, the differentiation of OC and OB needs to be tightly regulated to maintain the balance between bone formation and destruction. The results of Example 1 show a significant effect of complement on both OC and OB differentiation, which can then have a profound effect on bone balance, depending upon which cell type is more severely affected. The results of Example 1 also strongly indicate that the inhibition of OCs by complement deprivation has a more profound impact on bone balance than the diminished osteogenic potential of MSCs, thus leading to a decreased bone loss in C3$^{-/-}$ mice. In addition, our in vitro data suggest that the alternative pathway of complement activation is important for the complement mediated effects on OC differentiation.

Bone Balance in C3$^{-/-}$ Mice after OVX

C3$^{-/-}$ mice were used to conduct studies into the possible role of complement in OC and OB differentiation and in in vivo bone homeostasis. OVX-induced osteoporosis in mice is a well-established animal model of post-menopausal osteoporosis, in which estrogen deprivation results in increased OC and OB numbers with OCs playing a more dominant role, thus leading to net bone loss. To determine if complement affects bone homeostasis in this model, WT and C3$^{-/-}$ mice were OVXed and, after 6 weeks, were anesthetized, their femurs imaged by microCT, and the acquired images analyzed for multiple bone parameters (Table 1). The results indicate a clear bone sparing effect in the C3$^{-/-}$ mice. For example, skeletal connectivity (Skel. Conn.) in the WT mice was down to only one third that of C3$^{-/-}$ mice, and trabecular thickness (Tb.Th.) and bone volume (Bone Vol.) were all significantly lower in WT than C3$^{-/-}$ mice. Only trabecular number (Tb.-Num.) did not rise to the level of significance, but still showed a trend (p=0.09), again, with C3$^{-/-}$ showing greater Tb.-Num than WT. The bone mineral density and bone mineral content parameters showed similar results where, in 3 out of 4 cases where the data reached significance, the C3$^{-/-}$ mice showed greater mineral content or mineral density than did WT mice.

TABLE

Table 1: Micro CT Bone Parameter Analysis

| Parameter | C3$^{-/-}$ | WT | P value |
|---|---|---|---|
| Skel. Conn. | 114.3 ± 15.4 | 54.6 ± 2.4 | 0.002 |
| Tb. Th. | 81.5 ± 3.3 | 61.7 ± 11.7 | 0.005 |

TABLE-continued

Table 1: Micro CT Bone Parameter Analysis

| Parameter | $C3^{-/-}$ | WT | P value |
|---|---|---|---|
| Bone Vol. | 0.73 ± 0.92 | 0.48 ± 0.11 | 0.002 |
| Tb. Num. | 3.00 ± 0.21 | 2.25 ± 0.82 | 0.09 NS |
| Med. BMD | 188.4 ± 9.0 | 148.4 ± 9.5 | <0.001 |
| Med BMC | 0.80 ± 0.07 | 0.62 ± 0.05 | 0.005 |
| Tr. BMC | 0.25 ± 0.03 | 0.17 ± 0.03 | 0.006 |

BMD = Bone Mineral Density;
BMC = Bone Mineral Content;
Conn = Connectivity;
Tr = Trabecular;
Th = thickness;
Num = number;
Med = Medullary (entire cavity volume).
(n = 3 in each group)

In vitro Effect of Complement Deficiency on OC Differentiation

We showed in Example 1 the impact of complement on OC formation in vitro using both mouse and human cells. In this study, the effect of complement on OC differentiation was investigated using WT and mice deficient in C3, factor D and C3aR/C5aR, and respective C3aR/C5aR antagonists. The results (Table 2) showed that BM cells from $C3^{-/-}$ and $C3aR^{-/-}$ $C5aR^{-/-}$ mice produced significantly fewer OCs than BM cells from WT, indicating that complement plays a significant role in OC formation. The role of C3aR/C5aR was confirmed in an experiment where WT BM cells were incubated in medium supplemented with C3aR and C5aR antagonists, which resulted in dramatically reduced OC numbers. The results also showed that $C3^{-/-}$ and $C3aR^{-/-}/C5aR^{-/-}$ BM cells produce reduced levels of IL-6, and that supplementing IL-6 into $C3^{-/-}$ BM cultures rescued the $C3^{-/-}$ phenotype, suggesting that complement regulates OC differentiation through C3aR/C5aR-driven IL-6 production. The studies using WT and factor $D^{-/-}$ BM cells showed that the deficiency of the alternative pathway of complement activation significantly reduces the numbers of differentiated TRAP+ OCs, indicating that at least in vitro, complement is activated through the alternative pathway to regulate OC differentiation (FIG. 2).

TABLE 2

Table 2: Complement regulates OC formation

| Bone Marrow Source | Trap+ Multi-Nucl. Cells/Well | Trap+ Mono-Nucl. Cells/Well |
|---|---|---|
| WT | 49 ± 10 | 230 ± 26 |
| $C3^{-/-}$ | 21 ± 6* | 119 ± 31* |
| WT | 50 ± 2 | 236 ± 16 |
| $C3aR^{-/-}C5aR^{-/-}$ | 20 ± 7* | 91 ± 10* |
| WT | 55 ± 29 | 226 ± 27 |
| WT + C3aR/C5aR Antagonists | 23 ± 12* | 159 ± 23* |
| $C3^{-/-}$ | 31 ± 4† | 108 ± 17† |
| $C3^{-/-}$ + IL-6 | 52 ± 9 | 249 ± 39 |

*p < 0.005 compared to WT
†p < 0.05 compared to IL-6 supplemented

In summary, these studies demonstrated that C3 deficiency protects mice from bone loss in a model of post-menopausal osteoporosis, and that the local BM cell-produced complement components have a significant impact on in vitro osteoclastogenesis, in which the alternative pathway of complement activation is important, and C3aR/C5aR-regulated IL-6 production plays a critical role. These results strongly suggest that complement directly regulates OC numbers and bone loss in osteoporosis through C3aR and/or C5aR.

EXAMPLE 3

Mechanisms by Which Complement Regulates OB Differentiation in Osteoporosis

In this Example we show C3aR and/or C5aR upregulate OB differentiation of MSCs by promoting Runx2 expression and inhibiting PPARy expression.

We examined each of the complement receptors on WT MSCs by flow cytometry following staining with rat anti-mouse CR1, CR2, CR3 or CR4 mAbs and with goat anti-mouse C5aR or C3aR Ab. These analyses showed that MSCs express both C5aR and C3aR but do not express detectable levels of CR1/CR2/CR3/CR4. As a result, we now focus on studying the effect of C5aR and C3aR on OB differentiation.

The complement components fB, fD, C3 and C5 are essential to generate C3a from C3, and C5a from C5 through the alternative pathway of complement activation. To test whether MSCs locally produce all these components, we isolated total RNA form WT MCCs and performed RT-PCR to test for the presence of transcripts of C3, fB, fD and C5. These analyses showed that MSCs do, indeed, express C3, fB, fD and C5. Complement functional assaysl using fB, fD or C5 deficient sera and MSC-conditioned media demonstrated that MSC locally produce functional fB, fD and C5 protein. Consequently, in principle, MSCs are fully capable of generating C5a and C3a through local complement activation.

$C3^{-/-}$MSCs are Less Efficient in Differentiating into OBs

To test whether complement modulates OB generation from MSCs, WT and $C3^{-/-}$ MSCs were exposed to osteoblastic differentiation conditions using established methods. After 3 weeks of OB differentiation, WT MSCs were highly positive for Alizarin Red S, indicative of OB mineral deposition; whereas $C3^{-/-}$ MSCs showed little if any Alizarin Red S positivity. To verify this result, we assayed the cells for alkaline phosphatase activity. Consistent with the Alizarin Red S staining, differentiated WT MSCs showed significant alkaline phosphatase activity (dark blue staining), while differentiated $C3^{-/-}$ MSCs were negative, indicating that complement locally produced by MSCs is required for efficient OB differentiation.

In contrast to decreased OB generation, $C3^{-/-}$ MSCs exhibited markedly greater adipocyte generation. At day 21 in adipogenic conditions, differentiated WT MSCs showed only scattered small adipocytes stained with Oil Red 0 while, under the identical conditions, $C3^{-/-}$ MSCs showed abundant Oil Red O- positivity.

$C3^{-/-}$ MSCs Failed to Increase Levels of Runx2 during OB Differentiation

Previous studies by others have shown that the runt-related transcription factor 2 (Runx2) is essential for MSC osteogenesis. To investigate the potential relationship between Runx2 expression and osteoblast differentiation in $C3^{-/-}$ mice, we next tested the expression levels of Runx2 in $C3^{-/-}$ and WT MSCs exposed to osteoblastic and adipogenic differentiation conditions in vitro. Total RNA was isolated from WT and MSCs at day 0 and day 20 in osteoblastic or adipocytic differentiation conditions and assayed by qRT-PCR. These analyses showed that under OB differentiation conditions WT MSCs had augmented Runx2 expression as reported previously (8.6 fold), while $C3^{-/-}$ MSCs failed to significantly upregulate Runx2 expression (1.1 fold).

From the above description of the invention, those skilled in the art will perceive improvements, changes and modifications Such improvements, changes and modifications are within the skill of the art and are intended to be covered by the appended claims. All publications, patents, and patent applications cited in the present application are herein incorporated by reference in their entirety.

Having described the invention, we claim:

1. A method of treating a degenerative bone condition in a subject in need thereof, the method comprising:
administering locally to hematopoietic progenitor cells or osteoclast progenitor cells a C3a receptor (C3aR) antagonist directed against C3aR, the C3aR antagonist being administered to the hematopoietic progenitor cells or osteoclast progenitor cells at an amount effective to inhibit osteoclast differentiation of the hematopoietic progenitor cells or osteoclast progenitor cells, the hematopoietic progenitor cells or osteoclast progenitor cells being in the subject or administered to the subject.

2. The method of claim 1, wherein the C3aR antagonist is an antibody directed against C3aR.

3. The method of claim 1, further comprising administering a C5aR antagonist to the hematopoietic progenitor cells or osteoclast progenitor cells, wherein the C5aR antagonist is an antibody directed against C5a receptor (C5aR).

4. The method of claim 1, the C3aR antagonist being administered locally to the hematopoietic progenitor cells or osteoclast progenitor cells at the site of the bone condition.

5. The method of claim 2, the C3aR antagonist being conjugated to a targeting moiety that targets hematopoietic progenitor cells or osteoclast progenitor cells.

6. The method of claim 1 wherein the bone condition comprises osteopenia or osteoporosis.

7. A method of treating post-menopausal osteoporosis in a subject in need thereof, the method comprising:
administering locally to hematopoietic progenitor cells or osteoclast progenitor cells a C3a receptor (C3aR) antagonist directed against C3aR, the C3aR antagonist being administered to the hematopoietic progenitor cells or osteoclast progenitor cells at an amount effective to inhibit osteoclast differentiation of the hematopoietic progenitor cells or osteoclast progenitor cells, the hematopoietic progenitor cells or osteoclast progenitor cells being in the subject or administered to the subject.

8. The method of claim 7, wherein the C3aR antagonist is an antibody directed against C3aR.

9. The method of claim 7, further comprising administering a C5aR antagonist to the hematopoietic progenitor cells or osteoclast progenitor cells, wherein the C5aR antagonist is an antibody directed against C5a receptor (C5aR).

10. The method of claim 7, the C3aR antagonist being administered locally to the hematopoietic progenitor cells or osteoclast progenitor cells of bone marrow of the subject.

11. The method of claim 8, the antibody being conjugated to a targeting moiety that targets hematopoietic progenitor cells or osteoclast progenitor cells of bone marrow of the subject.

12. A method of treating post-menopausal osteoporosis of a subject, the method comprising:
administering locally to bone marrow of the subject a C3a receptor (C3aR) antagonist directed against C3aR, the C3aR antagonist being administered locally to the bone marrow cells of the subject at an amount effective to inhibit osteoclast differentiation of hematopoietic progenitor cells or osteoclast progenitor cells.

13. The method of claim 12, wherein the C3aR antagonist is an antibody directed against C3aR.

14. The method of claim 12, further comprising administering a C5aR antagonist to the bone marrow, the C5aR antagonist is an antibody directed against C5aR.

15. The method of claim 1, wherein the method further comprises administering a STAT3/IL-6 signaling pathway antagonist to the subject.

16. The method of claim 1, further comprising administering a C5a receptor (C5aR) antagonist to the hematopoietic progenitor cells or osteoclast progenitor cells.

17. The method of claim 7, further comprising administering a C5a receptor (C5aR) antagonist to the hematopoietic progenitor cells or osteoclast progenitor cells.

18. The method of claim 12, further comprising administering a C5a receptor (C5aR) antagonist to the hematopoietic progenitor cells or osteoclast progenitor cells.

* * * * *